United States Patent
Mujica-Fernaud et al.

(10) Patent No.: US 9,876,171 B2
(45) Date of Patent: Jan. 23, 2018

(54) MATERIALS FOR ELECTRONIC DEVICES

(75) Inventors: Teresa Mujica-Fernaud, Darmstadt (DE); Christof Pflumm, Darmstadt-Arheilgen (DE); Irina Martynova, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 734 days.

(21) Appl. No.: 14/110,946

(22) PCT Filed: Mar. 15, 2012

(86) PCT No.: PCT/EP2012/001156
§ 371 (c)(1),
(2), (4) Date: Oct. 10, 2013

(87) PCT Pub. No.: WO2012/139692
PCT Pub. Date: Oct. 18, 2012

(65) Prior Publication Data
US 2014/0027755 A1    Jan. 30, 2014

(30) Foreign Application Priority Data
Apr. 13, 2011  (EP) ..................................... 11003106

(51) Int. Cl.
| | | |
|---|---|---|
| H01L 51/00 | (2006.01) | |
| C07D 471/14 | (2006.01) | |
| C07D 487/04 | (2006.01) | |
| C07D 487/22 | (2006.01) | |
| C07D 498/04 | (2006.01) | |
| C07D 513/04 | (2006.01) | |
| C07D 519/00 | (2006.01) | |
| H01L 51/50 | (2006.01) | |

(52) U.S. Cl.
CPC ........ *H01L 51/0035* (2013.01); *C07D 471/14* (2013.01); *C07D 487/04* (2013.01); *C07D 487/22* (2013.01); *C07D 498/04* (2013.01); *C07D 513/04* (2013.01); *C07D 519/00* (2013.01); *H01L 51/0036* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/0085* (2013.01); *H01L 51/5012* (2013.01); *Y02E 10/549* (2013.01)

(58) Field of Classification Search
CPC .............. C07D 487/04; H01L 51/0035; H01L 51/0067
See application file for complete search history.

(56) References Cited

U.S. PATENT DOCUMENTS

| | | | |
|---|---|---|---|
| 6,551,723 B1 | 4/2003 | Okada et al. | |
| 9,040,172 B2 | 5/2015 | Parham et al. | |
| 2007/0031699 A1* | 2/2007 | Yamada | ................. C08G 61/00 428/690 |
| 2008/0016934 A1 | 1/2008 | Grimm et al. | |
| 2010/0051928 A1* | 3/2010 | Fukuzaki | ............. C07D 471/16 257/40 |
| 2011/0315975 A1 | 12/2011 | Kai et al. | |
| 2012/0097899 A1 | 4/2012 | Parham et al. | |
| 2012/0241681 A1 | 9/2012 | Schaefer et al. | |
| 2013/0092922 A1 | 4/2013 | Stoessel et al. | |
| 2013/0270540 A1* | 10/2013 | Numata | ................. C09K 11/06 257/40 |

FOREIGN PATENT DOCUMENTS

| | | |
|---|---|---|
| JP | 2000063818 A | 2/2000 |
| JP | 2001160488 A | 6/2001 |
| JP | 2010-087496 A | 4/2010 |
| JP | 5-107705 B2 | 12/2012 |
| WO | WO-2010113726 A1 | 10/2010 |
| WO | WO-2011000455 A1 | 1/2011 |
| WO | WO-2011160757 A1 | 12/2011 |
| WO | WO-2012130709 A1 | 10/2012 |

OTHER PUBLICATIONS

Samsoniya et al. The chemistry of indoloindoles, Russian Chemical Reviews 76 (4) 313-326, 2007.*
Eric S. Sherman and Sherry R. Chemler, Copper(II)-Catalyzed Aminooxygenation and Carboamination of N-Aryl-2-allylanilines, Adv Synth Catal. Feb. 1, 2009; 351(3): 467.*
PubChem Compound Limits Advanced Search—Compound Summary for: CID 9928634.
International Search Report for PCT/EP2012/001156 dated Jun. 14, 2012.
Database Registry (Online), XP-002676517, (2001), 1 page.
Database Registry (Online), XP-002676518, (2000), 1 page.
Dolby, Lloyd J., et al., "2-Alkylidene-2H-Indole Intermediates. The Thermolysis of 2-Hydroxydiphenylmethylindole", The Journal of Organic Chemistry, vol. 34, No. 10, (1969), pp. 2988-2993.
Volovenko, Yu M., et al., "Synthesis of Condensed Pyrrolo[b]Pyrazines", Chemistry of Heterocyclic Compounds, vol. 35, No. 9, (1999), pp. 10891093.
Fursy, Tamara, et al., "Synthesis of Novel Heterocyclic Systems from a-(2-R-5-Halogenopyrimidin-4-yl)-2-Azahetarylacetonitriles. New Potential Anticancer Agents", Chemistry of Heterocyclic Compounds, (1998), 3 pages, XP009159618.
Caplus Database, XP-002676987, (1999), 2 pages.
Kawashima, Kenya, et al., "Synthesis of Dibenzo[b,f]Cycloprop[d]Azepine Derivatives. II. Introduction of a Cyclopropane Ring by the Dichloromethylene Transfer Reaction", Chem. Pharma. Bull., vol. 26, No. 3, (1978), pp. 942-950.
Barbero, Nekane, et al., "Divergent Synthesis of Isoindolo[2,1-a]indole and indolo[1,2-a]indole through Copper-Catalysed C- and N-Arylations", Tetrahedron Letters, vol. 50, (2009), pp. 2129-2131.

(Continued)

*Primary Examiner* — Alex A Rolland

(57) ABSTRACT

The present invention relates to an electronic device comprising one or more compounds of a formula (I) or (II). Furthermore, the invention encompasses the use of a compound of the formula (I) or (II) in an electronic device, and the provision of certain compounds of the formula (I) or (II).

13 Claims, No Drawings

(56) References Cited

OTHER PUBLICATIONS

Dolby et al., "2-Alkylidene-2H-indole Intermediates. The Thermolysis of 2- Hydroxydiphenylmethylindole", *J.Org. Chem.*, vol. 34, No. 10, pp. 2988-2993 (1969).
Volovenko et al, "Synthesis of Condensed Pyrrolo[b]Pyrazines", *Chemistry of Heterocyclic Compounds*, vol. 35, No. 9, pp. 1089-1093 (1999).
RN 308298-97-7 Registry (2000).
RN 327080-21-7 Registry (2001).
Rogness, D., et al., "Rapid synthesis of the indole-indolone scaffold via [3+2] annulation of arynes by methyl indole-2-carboxylates", Tetrahedron Letters, 2009, vol. 50, No. 28, pp. 4003-4008.
Sherman, E., et al., "Copper(II)-Catalyzed Aminooxgenation and Carboamination of N-Aryl-2-allylanilines", Advanced Synthesis & Catalysis, 2009, vol. 351, No. 3, pp. 467-471.

\* cited by examiner

MATERIALS FOR ELECTRONIC DEVICES

RELATED APPLICATIONS

This application is a national stage application (under 35 U.S.C. §371) of PCT/EP2012/001156, filed Mar. 15, 2012, which claims benefit of European Application No. 11003106.9, filed Apr. 13, 2011, which is incorporated by reference herein.

The present invention relates to an electronic device comprising one or more compounds of a formula (I) or (II) defined below. Furthermore, the invention encompasses the use of a compound of the formula (I) or (II) in an electronic device, and the provision of certain compounds of the formula (I) or (II) defined below.

The development of novel functional compounds for use in electronic devices is currently the subject of intense research. The aim here is the development and investigation of compounds which have hitherto not yet been employed in electronic devices, and the development of compounds which facilitate an improved property profile of the devices.

The term electronic device in accordance with the present invention is taken to mean, inter alia, organic integrated circuits (OSCs), organic field-effect transistors (OLETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

The structure of organic electroluminescent devices (OLEDs) in which the compounds of the formula (I) or (II) can preferably be employed as functional materials is known to the person skilled in the art and is described, inter alia, in U.S. Pat. No. 4,539,507, U.S. Pat. No. 5,151,629, EP 0676461 and WO 1998/27136.

Further improvements are still necessary with respect to the performance data of the organic electroluminescent devices, in particular with a view to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices.

In addition, it is desirable for the compounds for use as organic semiconductor materials to have high thermal stability and a high glass-transition temperature and to be sublimable without decomposition.

In this connection, there is, inter alia, a demand for alternative matrix materials for use in electronic devices. In particular, there is a demand for matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis(carbazolyl)biphenyl, are frequently used as matrix materials. There is still potential for improvement here, in particular with respect to the lifetime and glass-transition temperature of the materials. Furthermore, there is a need for improvement with respect to the operating voltage of the electronic devices comprising the materials in question.

Furthermore, ketones (WO 2004/093207), phosphine oxides, sulfones (WO 2005/003253) and triazine compounds, such as triazinylspirobifluorene (cf. the applications WO 2005/053055 and WO 2010/015306), are used as matrix materials for phosphorescent emitters. There is still potential for improvement here, in particular with respect to the efficiency and compatibility with metal complexes which contain ketoketonate ligands, for example acetylacetonate.

Furthermore, metal complexes, for example BAlq or zinc(II) bis[2-(2-benzothiazole)phenolate], are used as matrix materials for phosphorescent emitters. There is still a need for improvement here, in particular with respect to the operating voltage and chemical stability. Purely organic compounds are frequently more stable than these metal complexes. Thus, some of these metal complexes are sensitive to hydrolysis, which makes handling of the complexes more difficult.

Also of particular interest is the provision of alternative materials as matrix components of mixed-matrix systems. A mixed-matrix system in the sense of this application is taken to mean a system in which two or more different matrix compounds are used mixed together with one (or more) dopant compounds as the emitting layer. These systems are, in particular, of interest in the case of phosphorescent organic electroluminescent devices. For more detailed information, reference is made to the application WO 2010/108579. Compounds known from the prior art which may be mentioned as matrix components in mixed-matrix systems are, inter alia, CBP (biscarbazolylbiphenyl) and TCTA (tris-carbazolyltriphenylamine). However, there continues to be a demand for alternative compounds for use as matrix components in mixed-matrix systems. In particular, there is a demand for compounds which effect an improvement in the operating voltage, the power efficiency and the lifetime of the electronic devices.

Furthermore, there is a demand for alternative hole-transport materials for use in electronic devices. In the case of hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a demand for novel hole-transport materials which have high charge-carrier mobility, enabling thicker hole-transport layers to be achieved with only a slight increase in the operating voltage.

The applications WO 2010/136109 and WO 2011/000455 disclose indenocarbazole and indolocarbazole derivatives having different linking geometry of the indene or indole and carbazole units. The compounds are suitable for use as functional materials in organic electroluminescent devices, in particular as matrix materials for phosphorescent emitters and as electron-transport materials. However, there continues to be a demand for alternative compounds, in particular those by means of which a reduction in the operating voltage, an increase in the power efficiency and an increase in the lifetime can be achieved.

In the course of the present invention, it has been found that compounds of the formula (I) or (II) indicated below are highly suitable for use in electronic devices.

The present invention thus relates to an electronic device, comprising anode, cathode and at least one organic layer, where the organic layer comprises at least one compound of the formula (I) or (II)

formula (I)

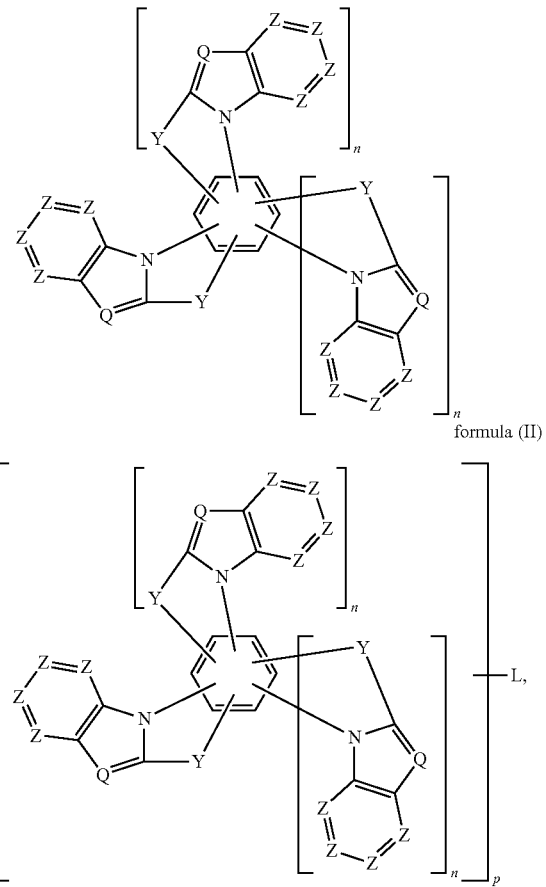

formula (II)

where:

Y is selected on each occurrence, identically or differently, from BR⁰, C(R¹)₂, Si(R¹)₂, NR⁰, PR⁰, P(=O)R⁰, O, S, S=O and S(=O)₂;

Q, Z are on each occurrence, identically or differently, CR¹ or N;

L is selected from C=O, C=NR¹, Si(R¹)₂, NR¹, P(=O)(R¹), O, S, SO, SO₂, alkylene groups having 1 to 20 C atoms or alkynylene or alkynylene groups having 2 to 20 C atoms, where one or more CH₂ groups in the said groups may be replaced by Si(R¹)₂, O, S, C=O, C=NR¹, C(=O)O, (C=O)NR¹, NR¹, P(=O)(R¹), SO or SO₂ and where one or more H atoms in the said groups may be replaced by D, F, Cl, Br, I, CN or NO₂, and aromatic or heteroaromatic ring systems having 5 to 60 aromatic ring atoms, which may in each case be substituted by one or more radicals R¹, and any desired combinations of 1, 2, 3, 4 or 5 identical or different groups selected from the above-mentioned groups; or L is a single bond, where p in this case is equal to 2;

R⁰ is on each occurrence, identically or differently, an aromatic or heteroaromatic ring system having 5 to 60 aromatic ring atoms, which may be substituted by one or more radicals R², or an aralkyl group or heteroaralkyl group having 5 to 60 aromatic ring atoms, which may be substituted by one or more radicals R²;

R¹ is on each occurrence, identically or differently, H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R² and where one or more CH₂ groups in the above-mentioned groups may be replaced by —R²C=CR²—, —C≡C—, Si(R²)₂, Ge(R²)₂, Sn(R²)₂, C=O, C=S, C=Se, C=NR², —C(=O)O—, —C(=O)NR²—, NR², P(=O)(R²), —O—, —S—, SO or SO₂ and where one or more H atoms in the above-mentioned groups may be replaced by D, F, Cl, Br, I, CN or NO₂, or an aromatic or heteroaromatic ring system having 5 to 60 aromatic ring atoms, which may in each case be substituted by one or more radicals R², or an aryloxy, heteroaryloxy, aralkyl or heteroaralkyl group having 5 to 60 aromatic ring atoms, which may be substituted by one or more radicals R², where two or more radicals R¹ may be linked to one another and may form a ring or a ring system;

R² is on each occurrence, identically or differently, H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R³ and where one or more CH₂ groups in the above-mentioned groups may be replaced by —R³C=CR³—, —C≡C—, Si(R³)₂, Ge(R³)₂, Sn(R³)₂, C=O, C=S, C=Se, C=NR³, —C(=O)O—, —C(=O)NR³—, NR³, P(=O)(R³), —O—, —S—, SO or SO₂ and where one or more H atoms in the above-mentioned groups may be replaced by D, F, Cl, Br, I, CN or NO₂, or an aromatic or heteroaromatic ring system having 5 to 60 aromatic ring atoms, which may in each case be substituted by one or more radicals R³, or an aryloxy, heteroaryloxy, aralkyl or heteroaralkyl group having 5 to 60 aromatic ring atoms, which may be substituted by one or more radicals R³, where two or more radicals R² may be linked to one another and may form a ring or a ring system;

R³ is on each occurrence, identically or differently, H, D, F or an aliphatic, aromatic and/or heteroaromatic organic radical having 1 to 20 C atoms, in which, in addition, one or more H atoms may be replaced by D or F; two or more substituents R³ here may also be linked to one another and form a ring or a ring system;

n is on each occurrence, identically or differently, 0 or 1, where, in the case n=0, the group in brackets is not present and optionally groups R¹ are instead bonded to the central benzene ring;

p is equal to 2, 3, 4, 5 or 6; and where the group Y and the nitrogen atom at any desired adjacent positions may be bonded to the aromatic six-membered ring;

where, in the formulae (I) and (II), in each case no or 1, 2 or 3 carbon atoms which are constituents of the central aromatic six-membered ring may be replaced by N if the sum of the indices n is equal to 0, and where, in the formulae (I) and (II), in each case no or 1 or 2 carbon atoms which are constituents of the central aromatic six-membered ring may be replaced by N if the sum of the indices n is equal to 1, and where, in formula (II), the moieties in square brackets with index p which are bonded to L may be identical or different; and
where, in formula (II), the group L may be bonded at any desired position of the moiety in square brackets with index p.

An aryl group in the sense of this invention contains 6 to 60 aromatic ring atoms; a heteroaryl group in the sense of this invention contains 1 to 60 C atoms at least one heteroatom, with the proviso that the sum of C atoms and heteratoms is at least 5. The heteroatoms are preferably selected from N, O and/or S.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aralkyl group in the sense of this invention is an alkyl group which is substituted by an aryl group, where the term aryl group is to be understood as defined above and the alkyl group has 1 to 20 C atoms, where individual H atoms and/or $CH_2$ groups in the alkyl group may also be replaced by the groups mentioned above under the definition of $R^1$ and $R^2$ and where the alkyl group represents the group which is bonded to the remainder of the compound. Correspondingly, a heteroaralkyl group represents an alkyl group which is substituted by a heteroaryl group, where the term heteroaryl group is to be understood as defined above and the alkyl group has 1 to 20 C atoms, where individual H atoms and/or $CH_2$ groups in the alkyl group may also be replaced by the groups mentioned above under the definition of $R^1$ and $R^2$ and where the alkyl group represents the group which is bonded to the remainder of the compound.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, the purposes of the present description, intended to be taken to mean, inter alia, that the two radicals are linked to one another by a chemical bond. This is illustrated by the following scheme:

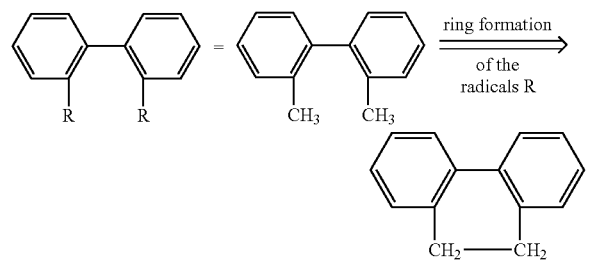

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

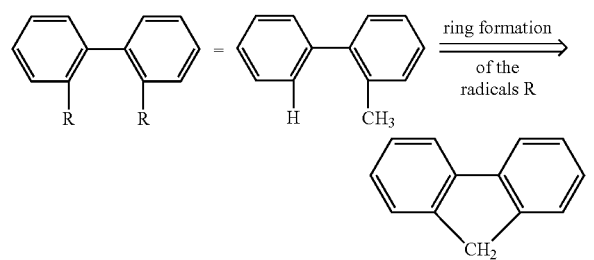

Furthermore, it should be emphasised that the bonds starting from N and Y drawn into the central benzene ring may emanate from any desired free position of the benzene. However, these must be adjacent positions, as indicated above in the definition of the compounds according to the invention.

It is not intended to be derived from the type of depiction in formula (I) and formula (II) that N must be bonded to the benzene ring above Y. The spatial arrangement of the indole derivative with the bridge Y can therefore be selected freely within the scope of the invention, so long as N and the group Y are bonded in adjacent positions.

Preferred embodiments for the bonding positions of Y and N are revealed by the preferred structures of compounds of the formula (I) or (II) depicted in a following section.

In accordance with the invention, the group L in compounds of the formula (II) can be bonded at any desired position of the moiety in square brackets with index p. The bonding preferably takes place to identical positions, i.e. symmetrically. The bonding furthermore preferably takes place via the positions marked with a circle below in the following formula (II), where, in the case of bonding via the central benzene ring, a maximum of one of the two indices n may be equal to 1.

Alternatively, bonding of L may also take place via a group Y.

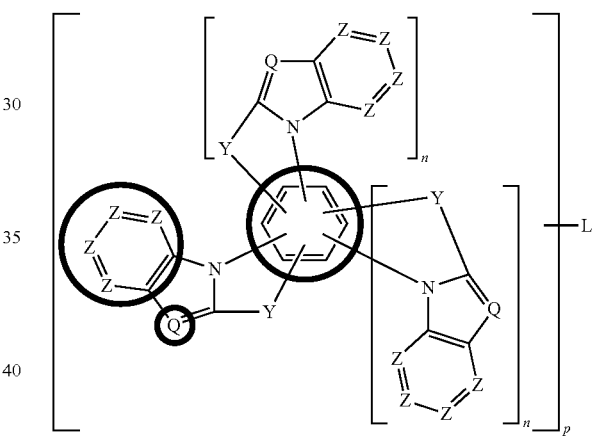

Preferred embodiments of formula (II) thus conform to the formulae (II-A) to (II-C)

formula (II-A)

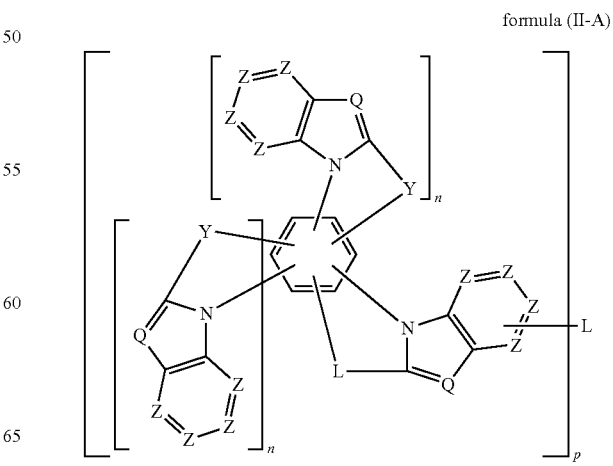

-continued

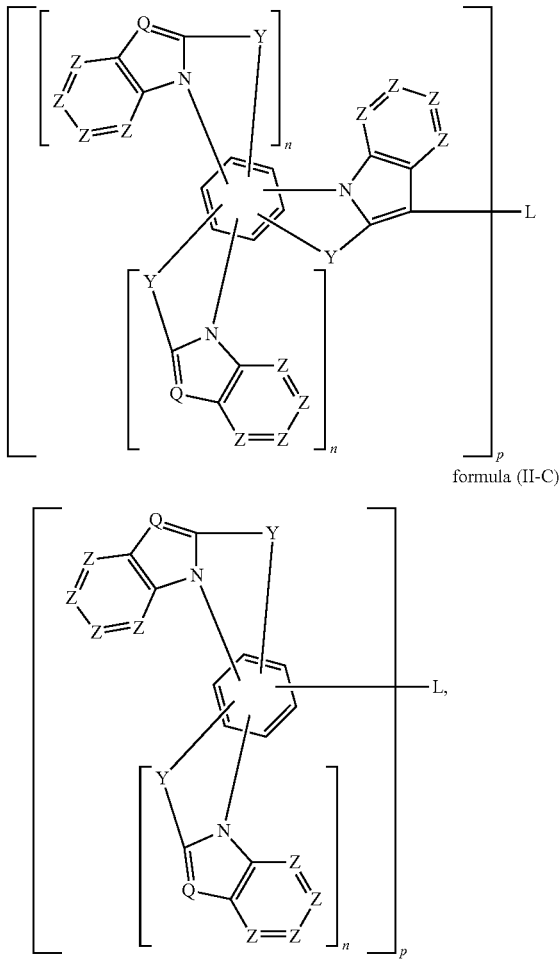

formula (II-B)

formula (II-C)

where, in formula (II-A), the group Z to which the group L is bonded stands for a carbon atom.

According to a further preferred embodiment, the moieties in square brackets with index p which are bonded to L in formula (II) are selected identically, i.e. the compound is symmetrical.

Furthermore, the index p, which indicates the number of moieties bonded to L, is preferably equal to 2 or 3 and particularly preferably equal to 2.

According to a preferred embodiment, the sum of the values for n in formula (I) is equal to 0 or 1, it is particularly preferably equal to 0. According to a preferred embodiment, the sum of the values for n per unit in square brackets with index p for formula (II) is equal to 0 or 1, particularly preferably equal to 0.

For the group Z, this is generally preferably equal to $CR^1$. Furthermore preferably, not more than 2 adjacent groups Z are equal to N. Furthermore preferably, 0, 1, 2 or 3, particularly preferably 0, 1 or 2, and very particularly preferably 0 or 1, Z per aromatic ring is equal to N.

It is furthermore preferred for the group Q to be equal to $CR^1$.

For the group Y, this is preferably selected on each occurrence, identically or differently, from $C(R^1)_2$, $NR^0$, O and S, particularly preferably from $C(R^1)_2$ and $NR^0$ and very particularly preferably from $C(R^1)_2$.

L is preferably selected from a single bond, where in this case p=2.

L is likewise preferably selected from C=O, $NR^1$, O or S, where in these cases p=2, or from alkylene groups having 1 to 10 C atoms, alkenylene groups having 2 to 10 C atoms, where one or more $CH_2$ groups in the said groups may be replaced by C=O, $NR^1$, P(=O)($R^1$), O or S, or from arylene or heteroarylene groups having 5 to 20 aromatic ring atoms, which may be substituted by one or more radicals $R^1$. The index p in these cases is preferably equal to 2, but may also be larger, for example 3.

L is likewise preferably a divalent aromatic or heteroaromatic ring system of the formula (L-1)

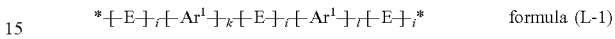  formula (L-1)

where p in this case is equal to 2 and where furthermore:
$Ar^1$ is on each occurrence, identically or differently, an aryl or heteroaryl group having 5 to 20 aromatic ring atoms, which may in each case be substituted by one or more radicals $R^1$;
E is on each occurrence, identically or differently, a single bond, C=O, $NAr^1$, P(=O)($R^1$), O, S, SO or $SO_2$;
i is on each occurrence, identically or differently, 0 or 1;
k, l are on each occurrence, identically or differently, 0, 1, 2 or 3, where the sum of the values of k and l is greater than 0; and
where furthermore the groups $Ar^1$ may be connected to one another via one or more divalent groups T, where
T is selected on each occurrence, identically or differently, from a single bond, $BR^1$, $C(R^1)_2$, C=O, C=S, C=$NR^1$, C=C($R^1)_2$, $CR^1$=$CR^1$, $Si(R^1)_2$, $NR^1$, $PR^1$, P(=O)$R^1$, O, S, S=O and S(=O)$_2$; and
the symbols * mark bonds from the group L to the remainder of the compound.
L is particularly preferably a single bond or an arylene or heteroarylene group having 5 to 18 aromatic ring atoms, which may be substituted by one or more radicals $R^1$, or a divalent aromatic or heteroaromatic ring system of the formula (L-1), where the index p is equal to 2 and where, restricting the definitions indicated above for formula (L-1),
E is on each occurrence, identically or differently, a single bond, C=O, $NAr^1$, O or S;
k, l is on each occurrence, identically or differently, 0 or 1, where the sum of the values of k and l is greater than 0; and
T is selected on each occurrence, identically or differently, from a single bond, $C(R^1)_2$, C=O, $NR^1$, O and S.

Furthermore preferably,
$R^0$ is on each occurrence, identically or differently, an aromatic or heteroaromatic ring system having 5 to 30 aromatic ring atoms, which may be substituted by one or more radicals $R^2$.

Particularly preferably,
$R^0$ is on each occurrence, identically or differently, an aryl or heteroaryl group having 5 to 20 aromatic ring atoms, which may be substituted by one or more radicals $R^2$.

Very particularly preferably,
$R^0$ is selected on each occurrence, identically or differently, from phenyl, naphthyl, pyridyl, pyrimidyl, pyrazinyl or triazinyl, which may be substituted by one or more radicals $R^2$.

Preferably,
$R^1$ is selected on each occurrence, identically or differently, from H, D, F, CN, $Si(R^2)_3$, $N(R^2)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals R² and where one or more CH₂ groups in the above-mentioned groups may be replaced by —C≡C—, —R²C═CR²—, Si(R²)₂, C═O, C═NR², —NR²—, —O—, —S—, —C(═O)O— or —C(═O)NR²—, or an aromatic or heteroaromatic ring system having 5 to 20 aromatic ring atoms, which may in each case be substituted by one or more radicals R², where two or more radicals R¹ may be linked to one another and may form a ring or a ring system.

Particularly preferably,

R¹ is selected on each occurrence, identically or differently, from H, D, F, N(R²)₂, a straight-chain alkyl group having 1 to 8 C atoms or a branched or cyclic alkyl group having 3 to 8 C atoms, where the above-mentioned groups may each be substituted by one or more radicals R² and where one or more CH₂ groups in the above-mentioned groups may be replaced by —R²C═CR²—, —NR²—, —O— or —S—, or an aryl or heteroaryl group having 5 to 20 aromatic ring atoms, which may in each case be substituted by one or more radicals R².

Preferably,

R² is selected on each occurrence, identically or differently, from H, D, F, CN, Si(R³)₃, N(R³)₂ or a straight-chain alkyl or alkoxy group having 1 to 20 C atoms or a branched or cyclic alkyl or alkoxy group having 3 to 20 C atoms, where the above-mentioned groups may each be substituted by one or more radicals R³ and where one or more CH₂ groups in the above-mentioned groups may be replaced by —C≡C—, —R³C═CR³—, Si(R³)₂, C═O, C═NR³, —NR³—, —O—, —S—, —C(═O)O— or —C(═O)NR³—, or an aromatic or heteroaromatic ring system having 5 to 20 aromatic ring atoms, which may in each case be substituted by one or more radicals R³, where two or more radicals R² may be linked to one another and may form a ring or a ring system.

Particularly preferably,

R² is selected on each occurrence, identically or differently, from H, D, F, N(R³)₂, a straight-chain alkyl group having 1 to 8 C atoms or a branched or cyclic alkyl group having 3 to 8 C atoms, where the above-mentioned groups may each be substituted by one or more radicals R³ and where one or more CH₂ groups in the above-mentioned groups may be replaced by —R³C═CR³—, —NR³—, —O— or —S—, or an aryl or heteroaryl group having 5 to 20 aromatic ring atoms, which may in each case be substituted by one or more radicals R³.

It is furthermore preferred for the compounds according to the invention to carry, as substituent R¹, at least one group selected from groups R¹-I, R¹-II and R¹-III, for which:

R¹-I is a heteroaryl group having 5 to 20 aromatic ring atoms or a keto group or a phosphorus oxide group or a sulfur oxide group, each of which is bonded directly or via one or more divalent aryl or heteroaryl groups and which may be substituted by one or more radicals R²;

R¹-II is an aromatic or heteroaromatic ring system having 5 to 24 aromatic ring atoms, which may be substituted by one or more radicals R², and R¹-III is an arylamine group, which may be substituted by one or more radicals R².

A keto group which is bonded directly or via one or more divalent aryl groups and which may be substituted by a radical R² is for the purposes of the present invention taken to mean a group of the following formula

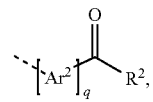

where the dashed bond represents the bonding site of the keto group, q can be equal to 0, 1, 2, 3, 4 or 5, Ar² represents on each occurrence, identically or differently, an aryl or heteroaryl group having 5 to 20 aromatic ring atoms, which may be substituted by one or more radicals R², where the groups Ar² may be connected to one another via one or more groups U; and U is selected on each occurrence, identically or differently, from a single bond, BR², C(R²)₂, C═O, C═S, C═NR², C═C(R²)₂, CR²═CR², Si(R²)₂, NR², PR², P(═O)R², O, S, S═O and S(═O)₂; and R² is as defined above.

A phosphorus oxide group which is bonded directly or via one or more divalent aryl groups and which may be substituted by a radical R² is for the purposes of the present invention taken to mean a group of the following formula

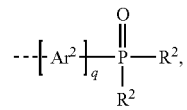

where the dashed bond represents the bonding site of the phosphorus oxide group and R², q and Ar² are as defined above, where the groups Ar² may be connected to one another via one or more groups U, as defined above.

A sulfur oxide group which is bonded directly or via one or more divalent aryl groups and which may be substituted by a radical R² is for the purposes of the present invention taken to mean a group of the following formula

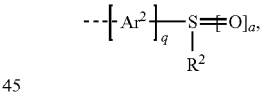

where the dashed bond represents the bonding site of the sulfur oxide group, a can be equal to 1 or 2, and R², q and Ar² are as defined above, where the groups Ar² may be connected to one another via one or more groups U, as defined above.

The above-mentioned groups R¹-I preferably represent groups of the following formula

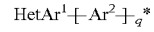

where the symbol * marks the bond to the remainder of the compound and furthermore q and Ar² are as defined above, where the groups Ar² may be connected to one another via one or more groups U, as defined above; and HetAr¹ represents a heteroaryl group having 5 to 20 aromatic ring atoms, which may be substituted by one or more radicals R².

HetAr¹ is preferably selected from pyridine, pyrimidine, pyridazine, pyrazine, triazine and benzimidazole, each of which may be substituted by one or more radicals R².

The above-mentioned groups R¹-II are preferably selected from phenyl, naphthyl, anthracenyl, phenanthrenyl, benzanthracenyl, pyrenyl, biphenyl, terphenyl and quaterphenyl, each of which may be substituted by one or more radicals R².

The above-mentioned groups R¹-III preferably represent groups of the following formula where the symbol * marks the bond to the remainder of the compound and furthermore q and Ar² are as defined above, where the groups Ar² may be connected to one another via one or more groups U, as defined above.

Particularly preferred embodiments of compounds of the formula (I) are the formulae depicted below:

formula (I-1)

formula (I-2)

formula (I-3)

formula (I-4)

formula (I-5)

formula (I-6)

formula (I-7)

where the symbols occurring are as defined above and furthermore the compounds may be substituted by radicals R¹ at all unsubstituted positions.

Very particular preference is given to compounds of the formulae (I-1), (I-2) and (I-3).

Particularly preferred embodiments of compounds of the formula (II-A), (II-B) and (II-C) are the formulae depicted below:

formula (II-A-1)

-continued
formula (II-A-2)
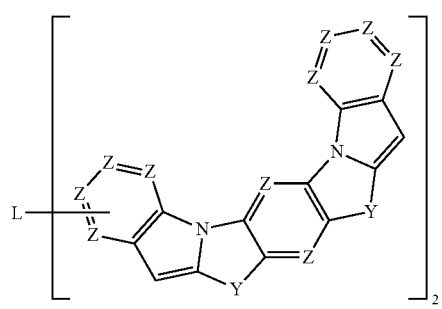
formula (II-A-3)
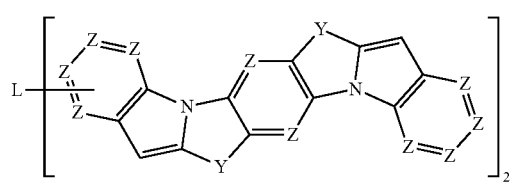
formula (II-A-4)
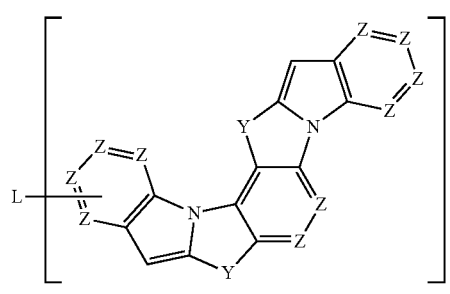
formula (II-A-5)
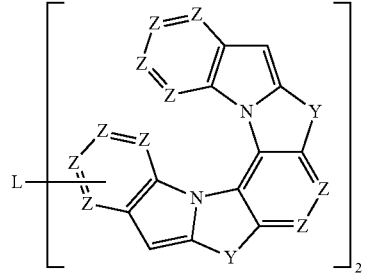
formula (II-A-6)
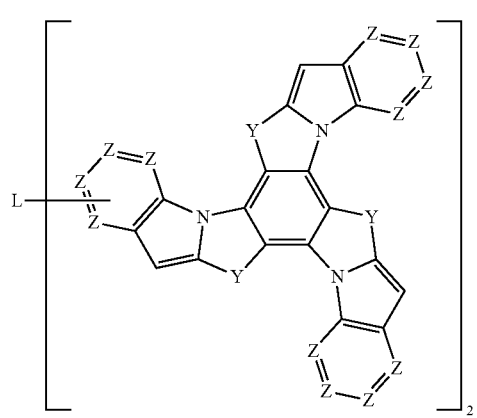
formula (II-A-7)
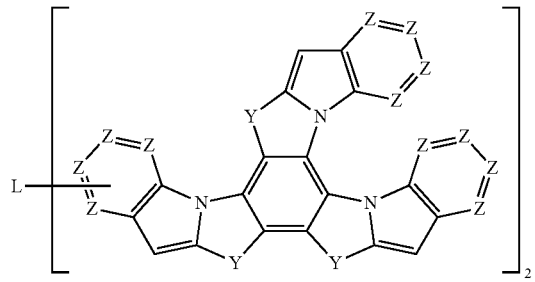
formula (II-B-1)
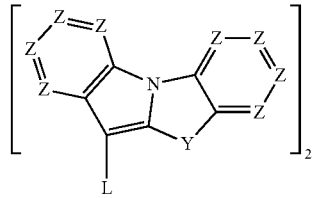
formula (II-B-2)
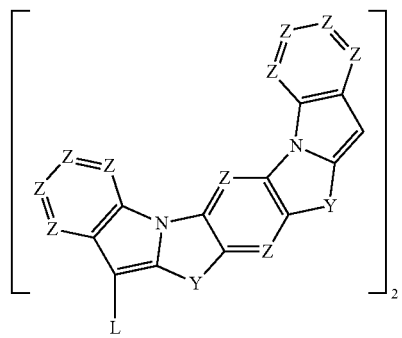
formula (II-B-3)
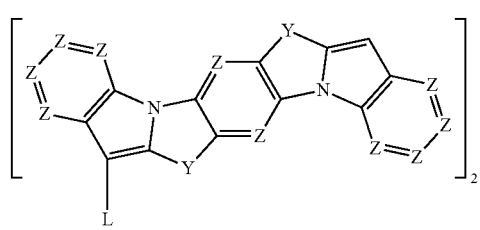
formula (II-B-4)
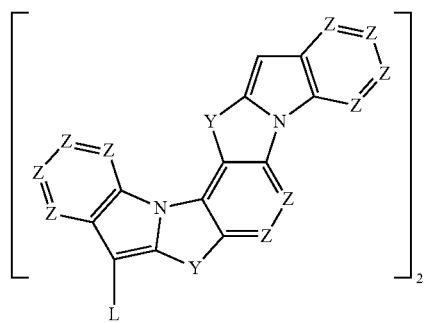

formula (II-B-5)

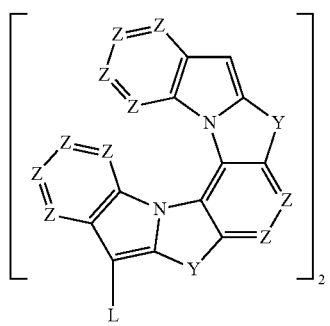

formula (II-B-6)

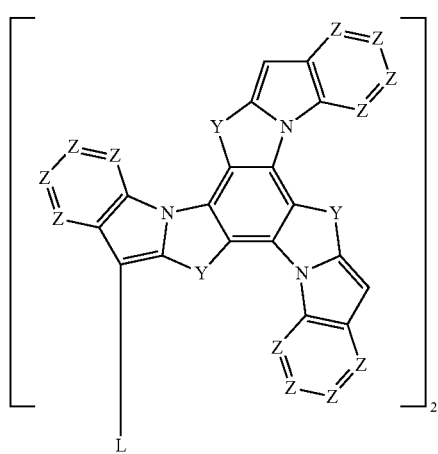

formula (II-B-7)

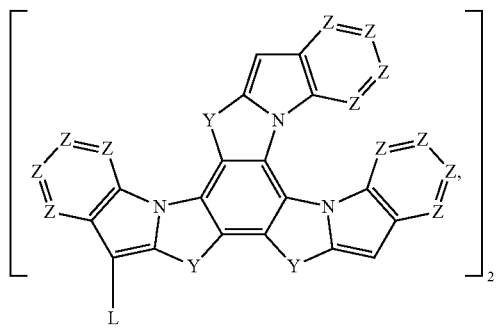

formula (II-C-1)

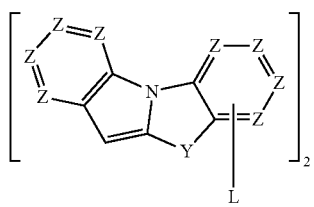

formula (II-C-2)

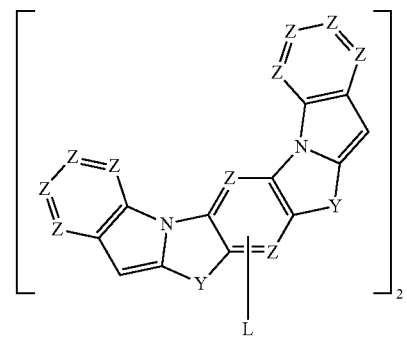

formula (II-C-3)

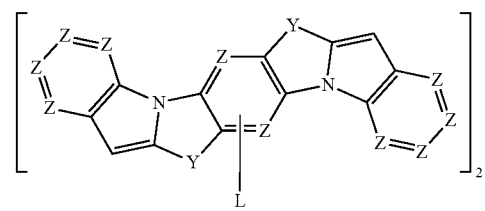

formula (II-C-4)

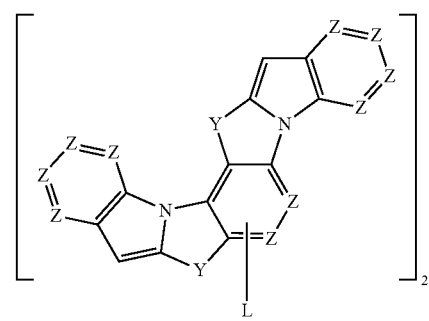

formula (II-C-5)

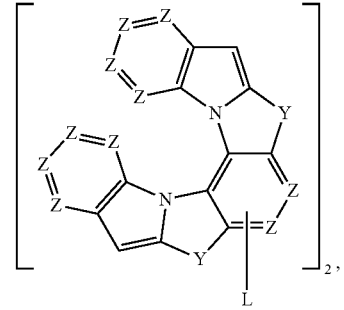

where the symbols occurring are as defined above and the group Z to which the group L is bonded stands for a carbon atom, and where furthermore the compounds may be substituted by radicals $R^1$ at all unsubstituted positions.

For the compounds of the formulae (II-A-1) to (II-A-7), (II-B-1) to (II-B-7) and (II-C-1) to (II-C-5), the preferred embodiments indicated above for the variable groups generally apply.

In particular, it is preferred for these compounds for no or 1 or 2 groups Z per aromatic ring to be equal to N.

Furthermore, it is preferred for these compounds for Y to be selected from $C(R^1)_2$, $NR^0$, O and S.

It is again furthermore preferred for these compounds for L to be a single bond or to be selected from C=O, $NR^1$, O, S, alkylene groups having 1 to 10 C atoms or alkenylene groups having 2 to 10 C atoms, where one or more CH$_2$ groups in the said groups may be replaced by C=O, NR$^1$, P(=O)(R$^1$), O or S, or arylene or heteroarylene groups having 5 to 20 aromatic ring atoms, which may be substituted by one or more radicals R$^1$, or aromatic or heteroaromatic ring systems of the formula (L-1).

Particular preference is given to compounds of the formulae (II-A-1), (II-A-2), (II-A-3), (II-B-1), (II-B-2) and (II-B-3).

Still greater preference is given to compounds of the following formulae

-continued formula (II-C-1-d)

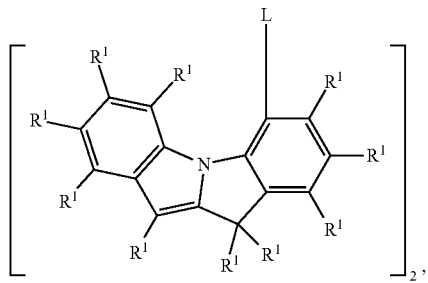

where R¹ and L are as defined above.

For the compounds of the formulae (I-1-a) to (I-1-c), (II-A-1-a) to (II-A-1-d), (II-B-1-a) and (II-C-1-a) to (II-C-1-d), the preferred embodiments indicated above for the variable groups generally apply.

It is especially preferred for the said compounds for them to carry, as substituent R¹, at least one group selected from groups R¹-I to R¹-III defined above.

It is again furthermore preferred for these compounds for L to be a single bond or to be selected from C=O, NR¹, O, S, alkylene groups having 1 to 10 C atoms or alkenylene groups having 2 to 10 C atoms, where one or more CH₂ groups in the said groups may be replaced by C=O, NR¹, P(=O)(R¹), O or S, or arylene or heteroarylene groups having 5 to 20 aromatic ring atoms, which may be substituted by one or more radicals R¹, or aromatic or heteroaromatic ring systems of the formula (L-1).

Of the said compounds, particular preference is given to compounds of the formulae (I-1-a), (I-1-b), (II-A-1-b), (II-B-1-a) and (II-C-1-b).

Examples of compounds according to the invention are shown in the following table:

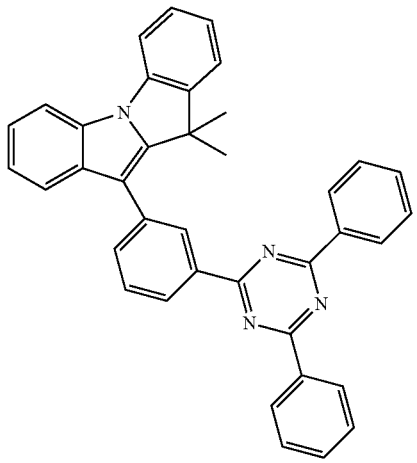

1

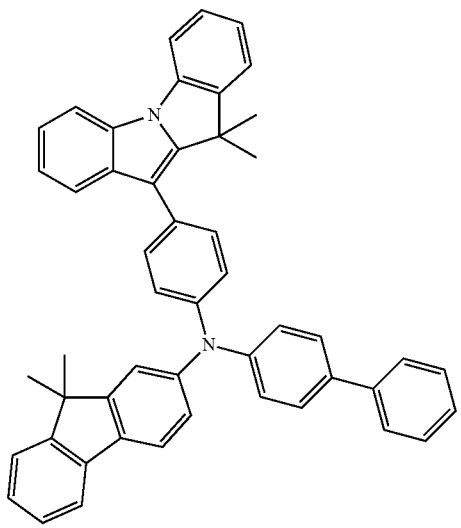 [SMILES: CC1(C)c2ccccc2-c2ccc(N(c3ccc(-c4ccccc4)cc3)c3ccc(-c4c5n(c6ccccc46)-c4ccccc4C5(C)C)cc3)cc21]

2

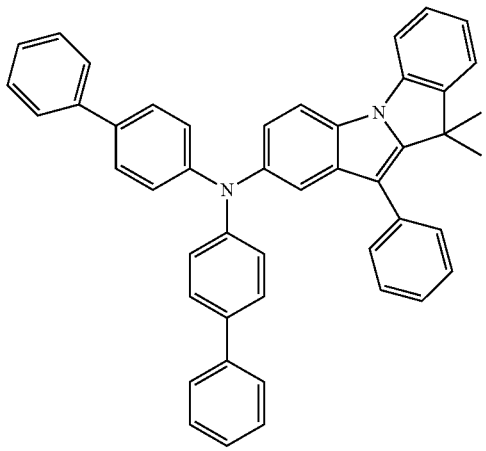 [SMILES: CC1(C)c2ccccc2-n2c1c(-c1ccccc1)c1cc(N(c3ccc(-c4ccccc4)cc3)c3ccc(-c4ccccc4)cc3)ccc12]
3
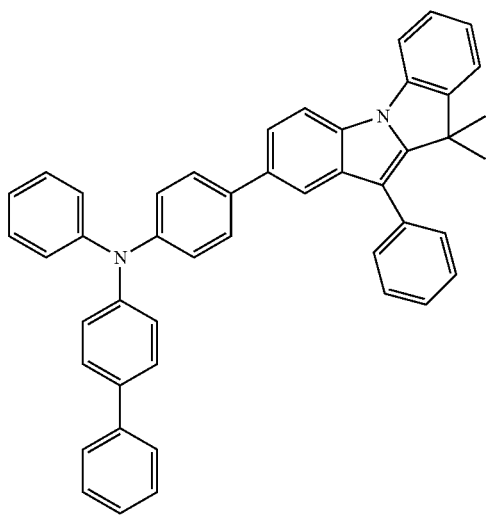 [SMILES: CC1(C)c2ccccc2-n2c1c(-c1ccccc1)c1cc(-c3ccc(N(c4ccccc4)c4ccc(-c5ccccc5)cc4)cc3)ccc12]
4
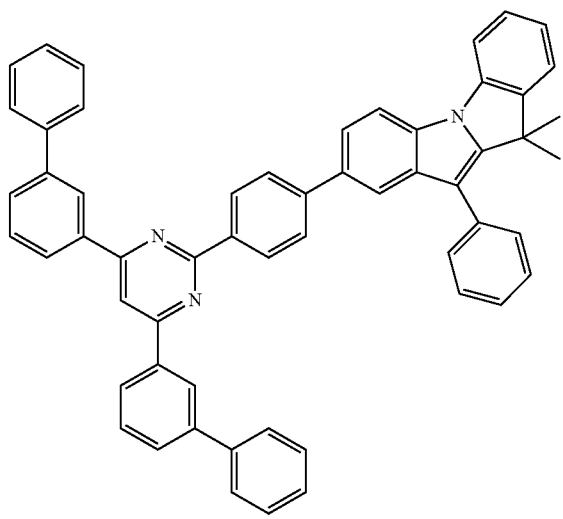 [SMILES: CC1(C)c2ccccc2-n2c1c(-c1ccccc1)c1cc(-c3ccc(-c4nc(-c5cccc(-c6ccccc6)c5)cc(-c5cccc(-c6ccccc6)c5)n4)cc3)ccc12]
5

-continued
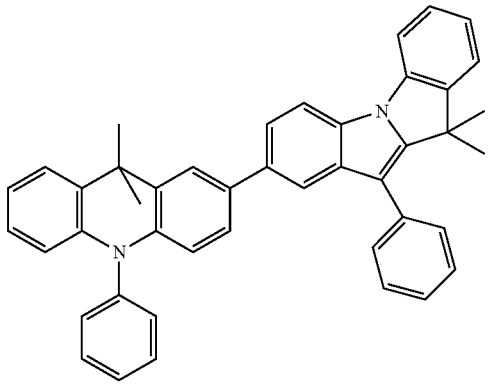
6
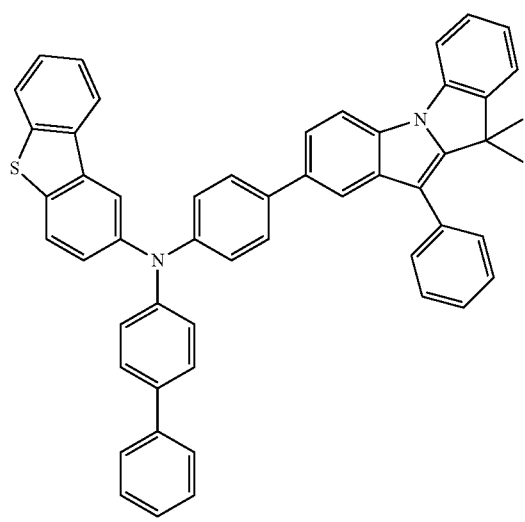 [SMILES: CC1(C)c2ccccc2-n2c1c(-c1ccccc1)c1cc(-c3ccc(N(c4ccc(-c5ccccc5)cc4)c4ccc5sc6ccccc6c5c4)cc3)ccc12]
7
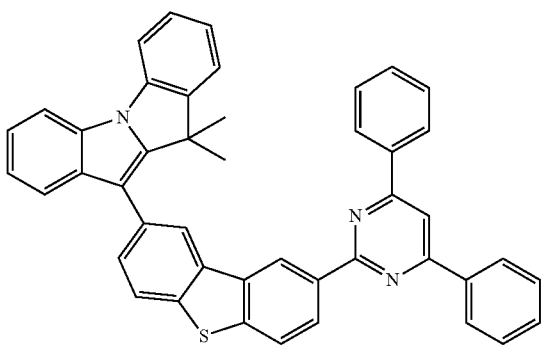 [SMILES: CC1(C)c2ccccc2-n2c1c(-c1ccc3sc4ccc(-c5nc(-c6ccccc6)cc(-c6ccccc6)n5)cc4c3c1)c1ccccc12]
8
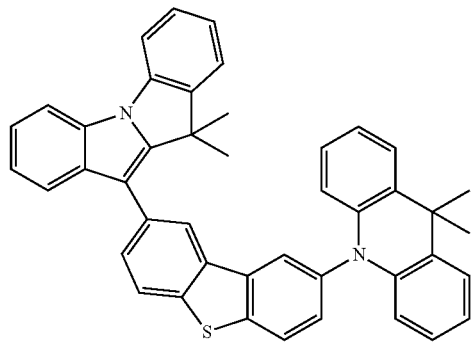 [SMILES: CC1(C)c2ccccc2N(c2ccc3sc4ccc(-c5c6n(c7ccccc57)-c5ccccc5C6(C)C)cc4c3c2)c2ccccc21]
9

-continued
10
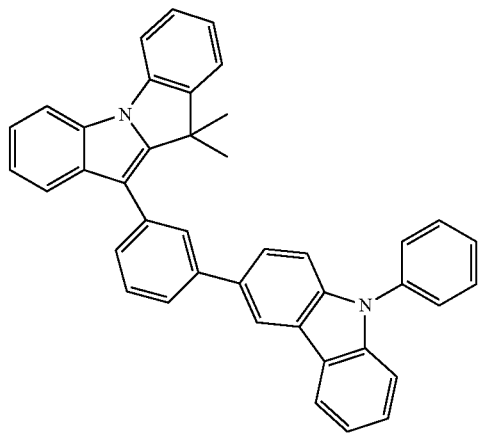 [SMILES: CC1(C)c2ccccc2-n2c1c(-c1cccc(-c3ccc4c(c3)c3ccccc3n4-c3ccccc3)c1)c1ccccc12]
11
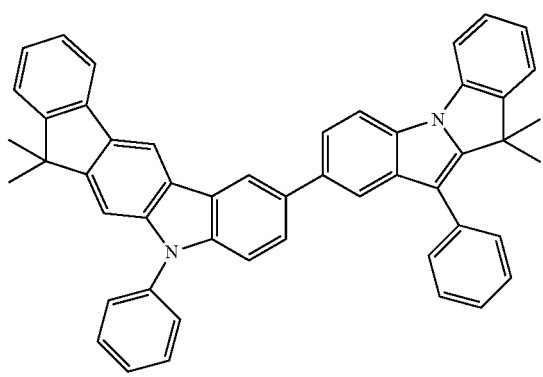
12
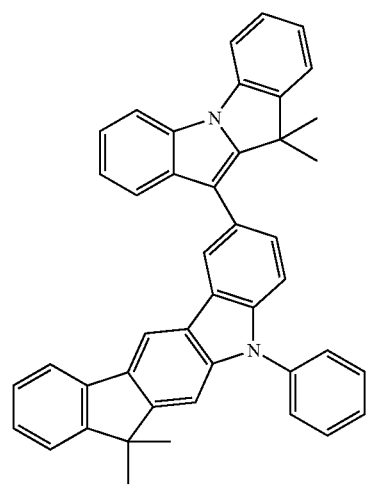 [SMILES: CC1(C)c2ccccc2-c2cc3c4cc(-c5c6n(c7ccccc57)-c5ccccc5C6(C)C)ccc4n(-c4ccccc4)c3cc21]

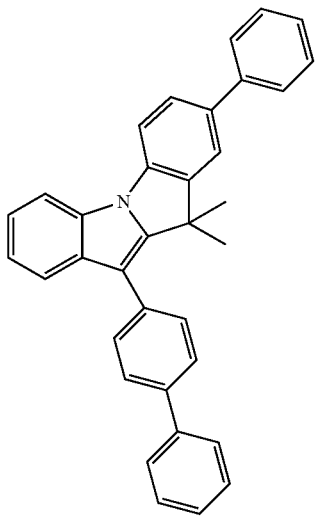 [SMILES: CC1(C)c2cc(-c3ccccc3)ccc2-n2c1c(-c1ccc(-c3ccccc3)cc1)c1ccccc12]
13
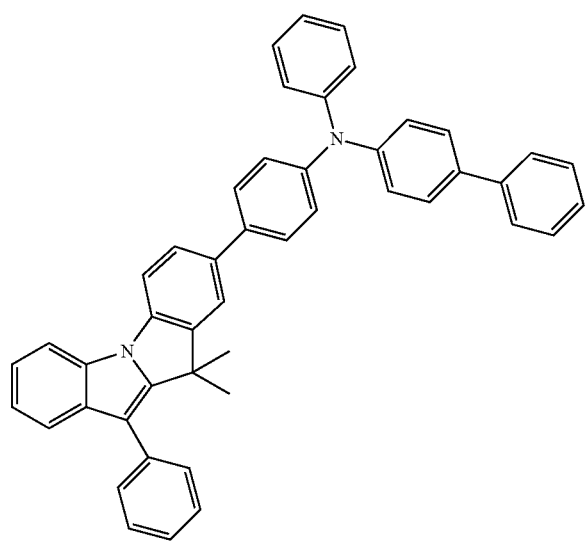 [SMILES: CC1(C)c2cc(-c3ccc(N(c4ccccc4)c4ccc(-c5ccccc5)cc4)cc3)ccc2-n2c1c(-c1ccccc1)c1ccccc12]
14
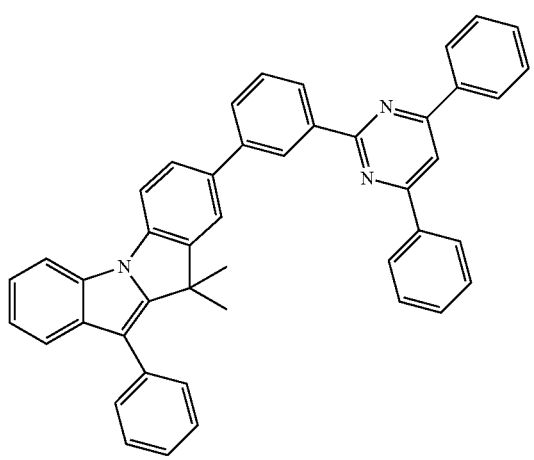 [SMILES: CC1(C)c2cc(-c3cccc(-c4nc(-c5ccccc5)cc(-c5ccccc5)n4)c3)ccc2-n2c1c(-c1ccccc1)c1ccccc12]
15

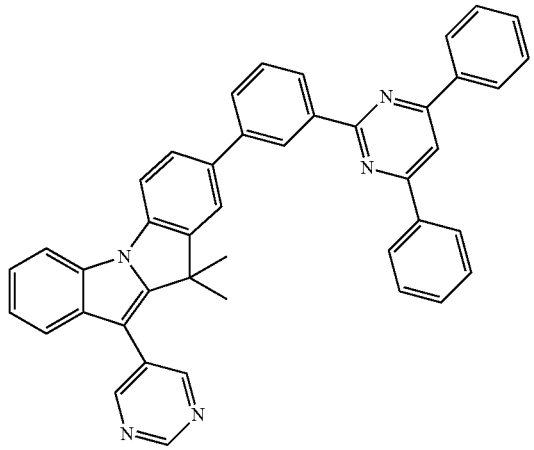
16
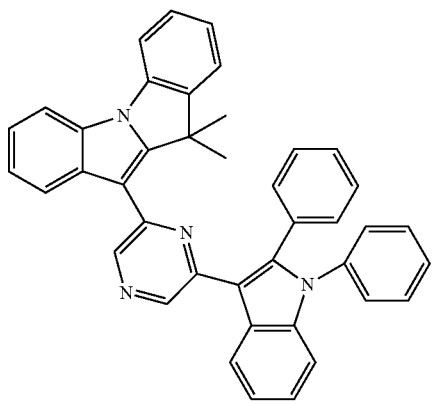 [SMILES: CC1(C)c2ccccc2-n2c1c(-c1cncc(-c3c(-c4ccccc4)n(-c4ccccc4)c4ccccc34)n1)c1ccccc12]
17
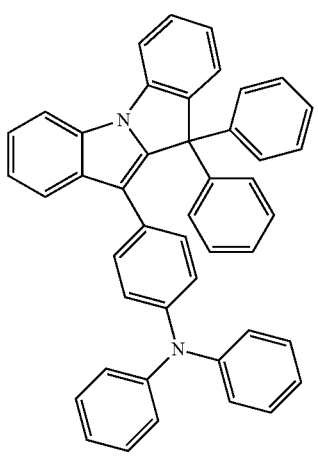 [SMILES: c1ccc(N(c2ccccc2)c2ccc(-c3c4n(c5ccccc35)-c3ccccc3C4(c3ccccc3)c3ccccc3)cc2)cc1]
18

-continued
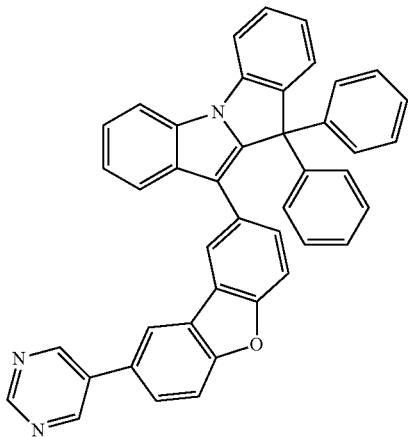 [SMILES: c1ccc(C2(c3ccccc3)c3ccccc3-n3c2c(-c2ccc4oc5ccc(-c6cncnc6)cc5c4c2)c2ccccc23)cc1]
19
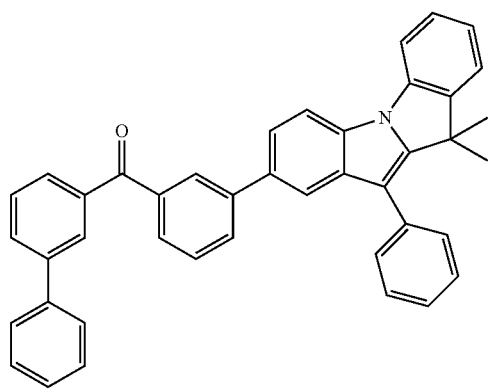 [SMILES: CC1(C)c2ccccc2-n2c1c(-c1ccccc1)c1cc(-c3cccc(C(=O)c4cccc(-c5ccccc5)c4)c3)ccc12]
20
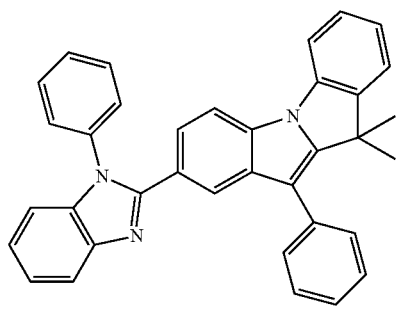 [SMILES: CC1(C)c2ccccc2-n2c1c(-c1ccccc1)c1cc(-c3nc4ccccc4n3-c3ccccc3)ccc12]
21
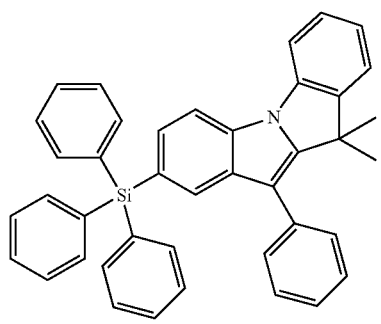 [SMILES: CC1(C)c2ccccc2-n2c1c(-c1ccccc1)c1cc([Si](c3ccccc3)(c3ccccc3)c3ccccc3)ccc12]
22

-continued
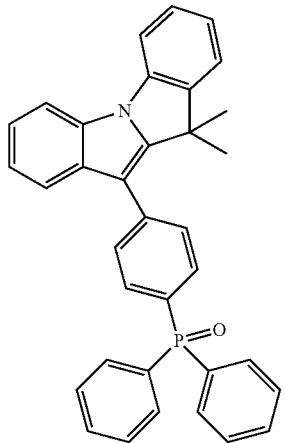 [SMILES: CC1(C)c2ccccc2-n2c1c(-c1ccc(P(=O)(c3ccccc3)c3ccccc3)cc1)c1ccccc12]
23
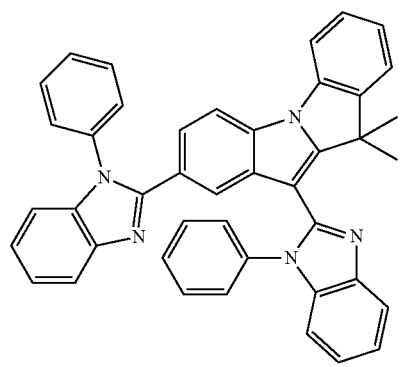 [SMILES: CC1(C)c2ccccc2-n2c1c(-c1nc3ccccc3n1-c1ccccc1)c1cc(-c3nc4ccccc4n3-c3ccccc3)ccc12]
24
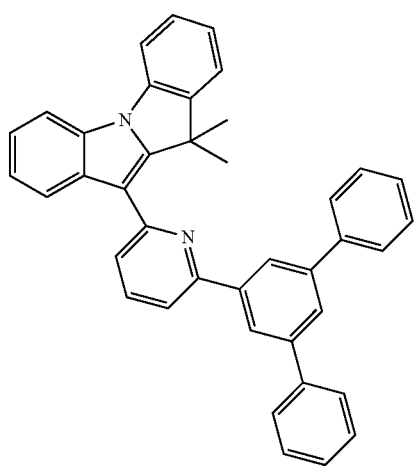 [SMILES: CC1(C)c2ccccc2-n2c1c(-c1cccc(-c3cc(-c4ccccc4)cc(-c4ccccc4)c3)n1)c1ccccc12]
25

26
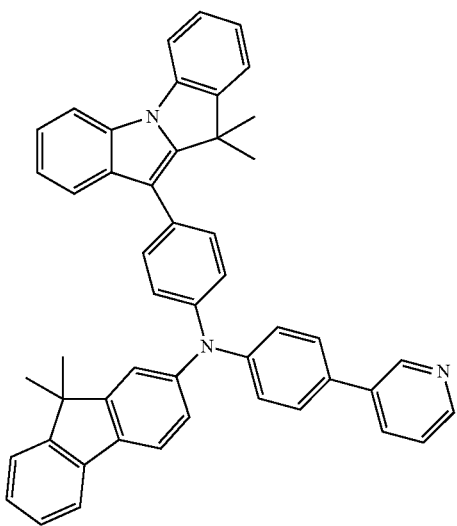 [SMILES: CC1(C)c2ccccc2-c2ccc(N(c3ccc(-c4cccnc4)cc3)c3ccc(-c4c5n(c6ccccc46)-c4ccccc4C5(C)C)cc3)cc21]
27
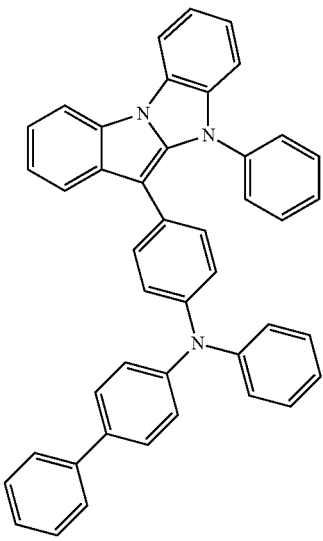 [SMILES: c1ccc(-c2ccc(N(c3ccccc3)c3ccc(-c4c5ccccc5n5c6ccccc6n(-c6ccccc6)c45)cc3)cc2)cc1]
28
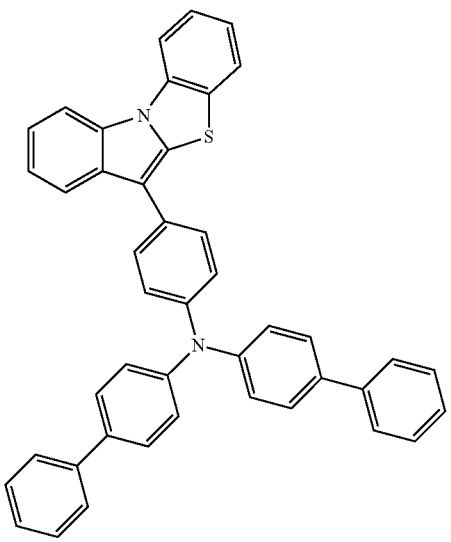 [SMILES: c1ccc(-c2ccc(N(c3ccc(-c4ccccc4)cc3)c3ccc(-c4c5ccccc5n5c4sc4ccccc45)cc3)cc2)cc1]

29
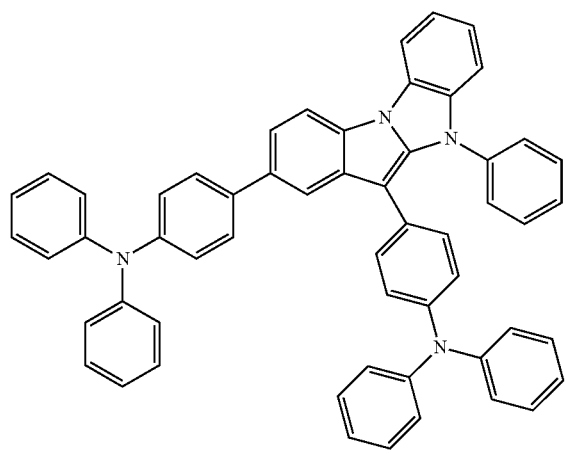 [SMILES: c1ccc(N(c2ccccc2)c2ccc(-c3ccc4c(c3)c(-c3ccc(N(c5ccccc5)c5ccccc5)cc3)c3n(-c5ccccc5)c5ccccc5n43)cc2)cc1]
30
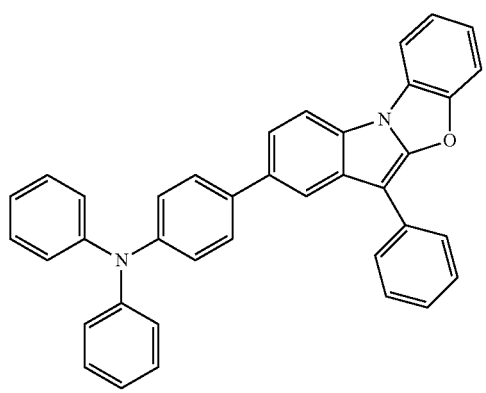 [SMILES: c1ccc(-c2c3cc(-c4ccc(N(c5ccccc5)c5ccccc5)cc4)ccc3n3c2oc2ccccc23)cc1]
31
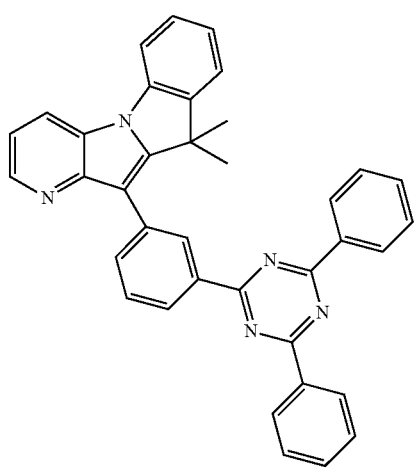 [SMILES: CC1(C)c2ccccc2-n2c1c(-c1cccc(-c3nc(-c4ccccc4)nc(-c4ccccc4)n3)c1)c1ncccc12]

32
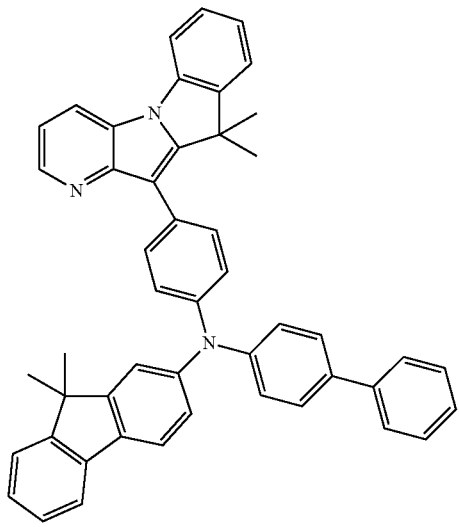
33
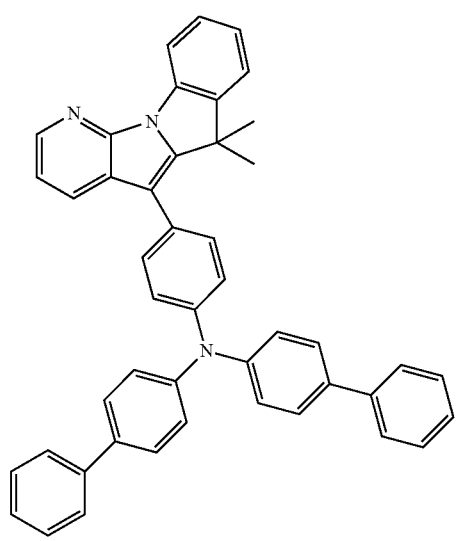 [SMILES: CC1(C)c2ccccc2-n2c1c(-c1ccc(N(c3ccc(-c4ccccc4)cc3)c3ccc(-c4ccccc4)cc3)cc1)c1cccnc12]
34
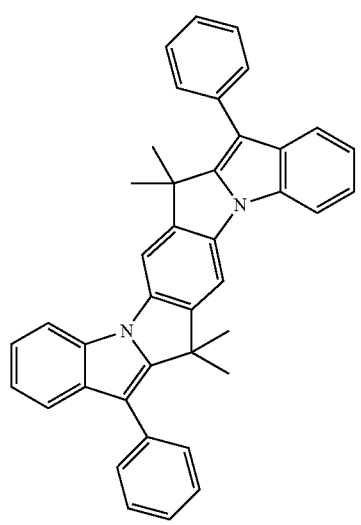 [SMILES: CC1(C)c2cc3c(cc2-n2c1c(-c1ccccc1)c1ccccc12)C(C)(C)c1c(-c2ccccc2)c2ccccc2n1-3]

35
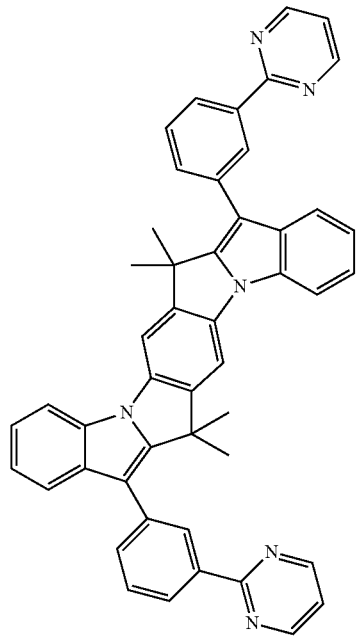 [SMILES: CC1(C)c2cc3c(cc2-n2c1c(-c1cccc(-c4ncccn4)c1)c1ccccc12)C(C)(C)c1c(-c2cccc(-c4ncccn4)c2)c2ccccc2n1-3]
36
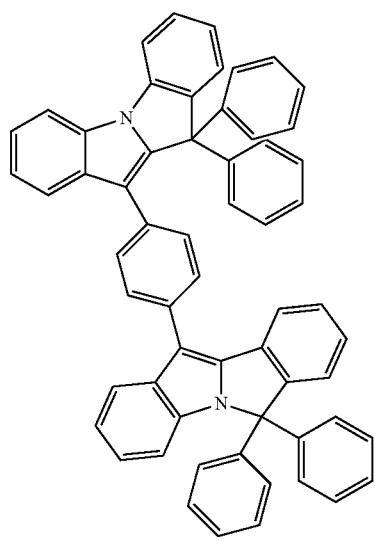 [SMILES: c1ccc(C2(c3ccccc3)c3ccccc3-n3c2c(-c2ccc(-c4c5n(c6ccccc46)C(c4ccccc4)(c4ccccc4)c4ccccc4-5)cc2)c2ccccc23)cc1]

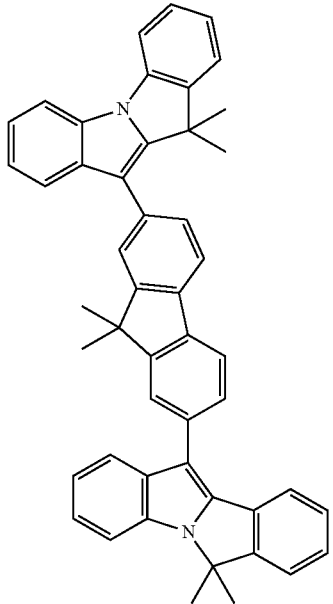 [SMILES: CC1(C)c2cc(-c3c4n(c5ccccc35)-c3ccccc3C4(C)C)ccc2-c2ccc(-c3c4n(c5ccccc35)C(C)(C)c3ccccc3-4)cc21]
37
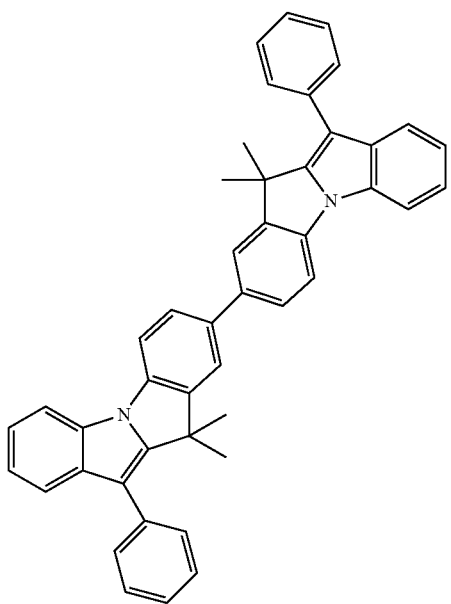 [SMILES: CC1(C)c2cc(-c3ccc4c(c3)C(C)(C)c3c(-c5ccccc5)c5ccccc5n3-4)ccc2-n2c1c(-c1ccccc1)c1ccccc12]
38

-continued
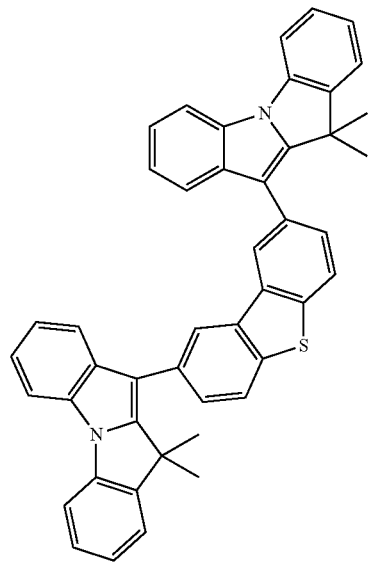 [SMILES: CC1(C)c2ccccc2-n2c1c(-c1ccc3sc4ccc(-c5c6n(c7ccccc57)-c5ccccc5C6(C)C)cc4c3c1)c1ccccc12]
39
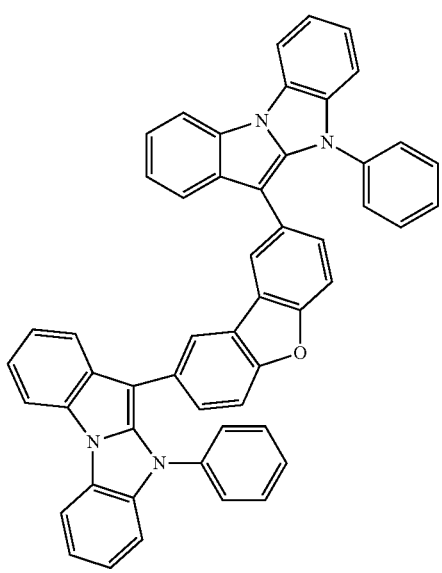 [SMILES: c1ccc(-n2c3ccccc3n3c4ccccc4c(-c4ccc5oc6ccc(-c7c8ccccc8n8c9ccccc9n(-c9ccccc9)c78)cc6c5c4)c23)cc1]
40
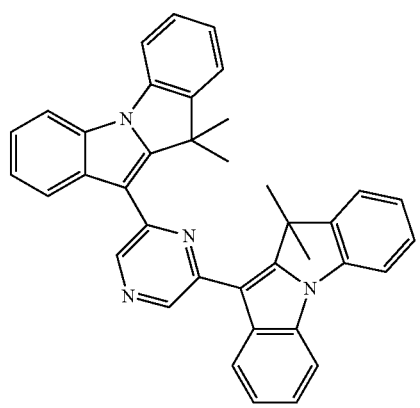
41

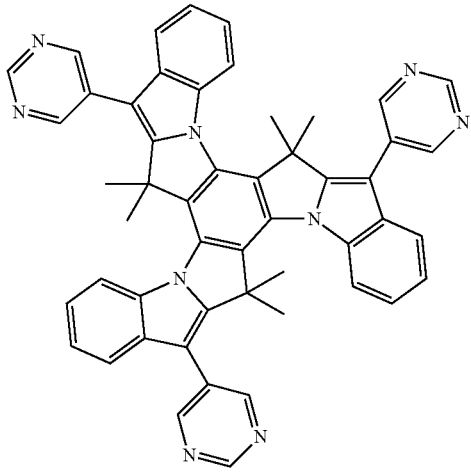 [SMILES: CC1(C)c2c3c(c4c(c2-n2c1c(-c1cncnc1)c1ccccc12)C(C)(C)c1c(-c2cncnc2)c2ccccc2n1-4)C(C)(C)c1c(-c2cncnc2)c2ccccc2n1-3]
42
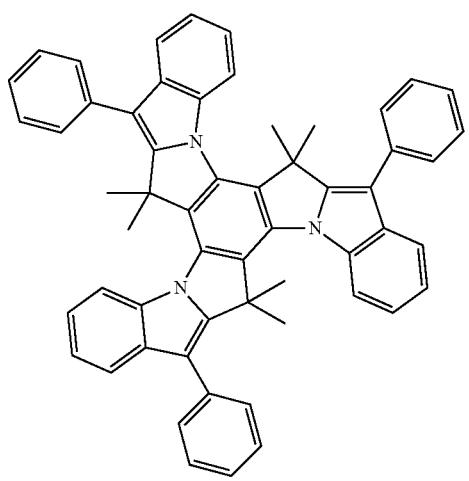 [SMILES: CC1(C)c2c3c(c4c(c2-n2c1c(-c1ccccc1)c1ccccc12)C(C)(C)c1c(-c2ccccc2)c2ccccc2n1-4)C(C)(C)c1c(-c2ccccc2)c2ccccc2n1-3]
43
The invention furthermore relates to a compound of the formula (I) or (II) in which the group Q is selected equal to $CR^1$, where the following compounds are excluded:
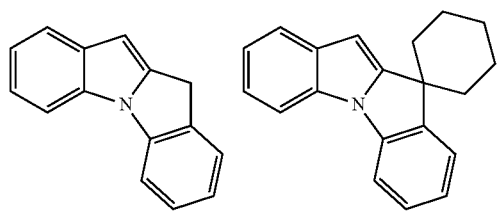
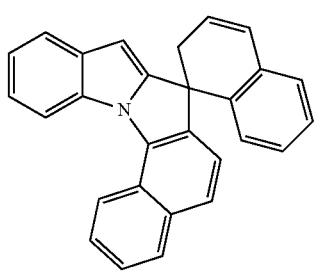

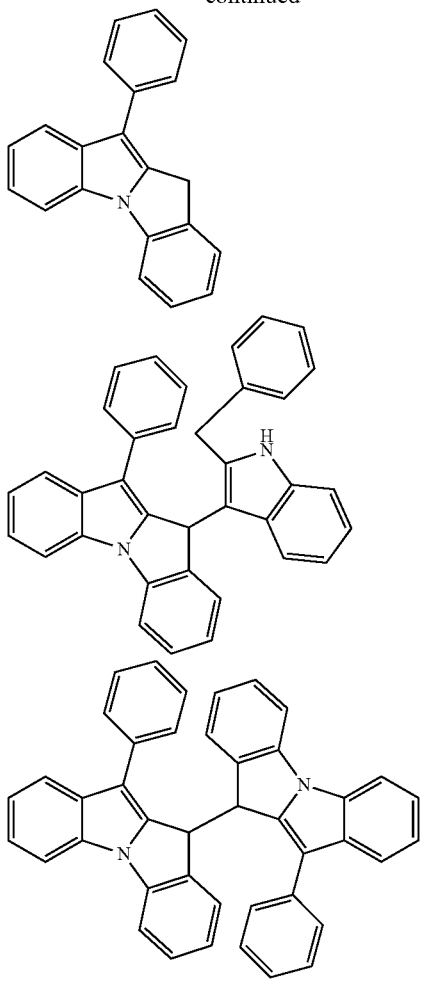

All embodiments of compounds which have been indicated as preferred above in connection with contents of the electronic device according to the invention are also preferred in relation to the inventive subject-matter of the compounds themselves.

In particular, the index p, which indicates the number of moieties bonded to L, is preferably equal to 2 or 3 and is particularly preferably equal to 2.

According to a preferred embodiment, the sum of the values for n in formula (I) is equal to 0 or 1, it is particularly preferably equal to 0. According to a preferred embodiment, the sum of the values for n per unit in square brackets with index p for formula (II) is equal to 0 or 1, particularly preferably equal to 0.

For the group Z, this is generally preferably equal to $CR^1$. Furthermore preferably, not more than 2 adjacent groups Z are equal to N. It is furthermore preferred for 0, 1, 2 or 3, particularly preferably 0, 1 or 2, and very particularly preferably 0 or 1, Z per aromatic ring to be equal to N.

For the group Y, this is preferably selected on each occurrence, identically or differently, from $C(R^1)_2$, $NR^0$, O and S, particularly preferably from $C(R^1)_2$ and $NR^0$ and very particularly preferably from $C(R^1)_2$.

The compounds according to the invention can be prepared by known organochemical synthetic methods. These include, for example, Ullmann coupling, Hartwig-Buchwald coupling, Suzuki coupling and brominations and cyclisations.

Scheme 1 below shows the synthesis of skeleton A, from which compounds according to the invention can be prepared via subsequent reactions.

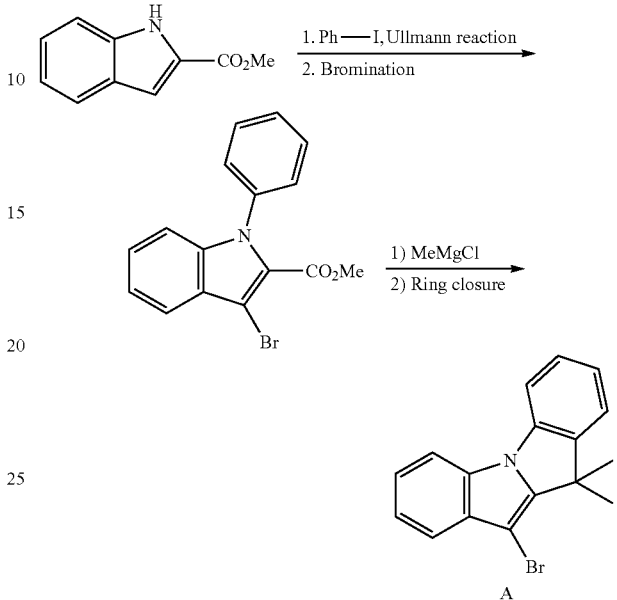

For the synthesis of skeleton A, firstly iodobenzene is coupled to methyl 1H-indolo-2-carboxylate in an Ullmann reaction. The resultant compound is then brominated by means of NBS. The reaction of the resultant compound with methylmagnesium chloride followed by a ring-closure reaction under dehydrating conditions gives the corresponding bridged indolophenyl derivative.

Scheme 2 shows the synthesis of skeleton B. It differs from the synthesis shown in Scheme 1 merely through the fact that, instead of iodobenzene, 1,4-diiodobenzene is employed in the Ullmann coupling with two equivalents of methyl 1H-indolo-2-carboxylate.

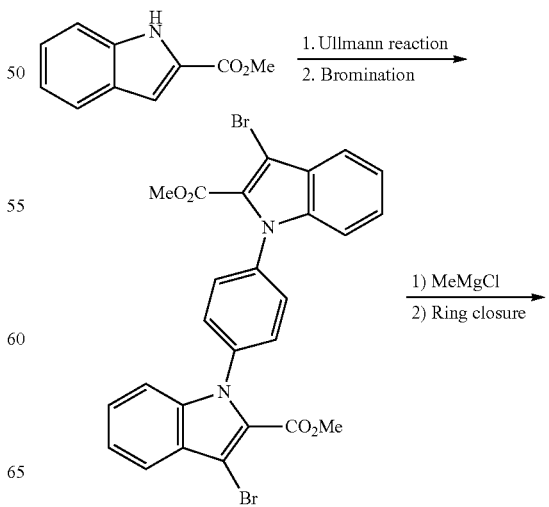

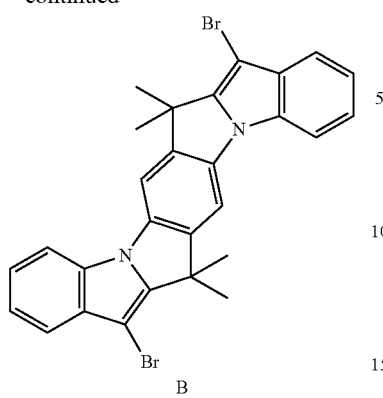

B

Scheme 3a shows by way of example for skeleton A various ways of obtaining compounds of the formula (I) according to the invention by derivatisation reactions. An analogous procedure can be used for skeleton B. In the first reaction shown, a Suzuki reaction is carried out with a monoborono-functionalised aryl derivative. In the second reaction shown, a corresponding diarylamine is introduced as substituent on the indole by a Buchwald reaction with a diarylamine.

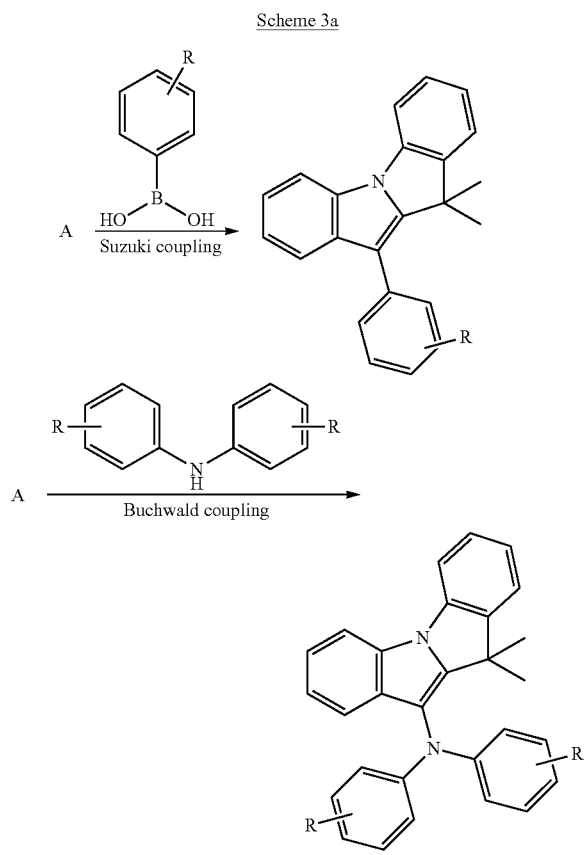

Scheme 3a

Scheme 3b shows by way of example how compounds of the formula (II) according to the invention can be obtained from intermediates of skeleton A. To this end, a bis-diborono-functionalised aryl derivative, shown for the example of 4,4'-diboronobiphenyl, is employed, so that a skeleton A is coupled to each of the two borono-substituted positions of the aryl derivative.

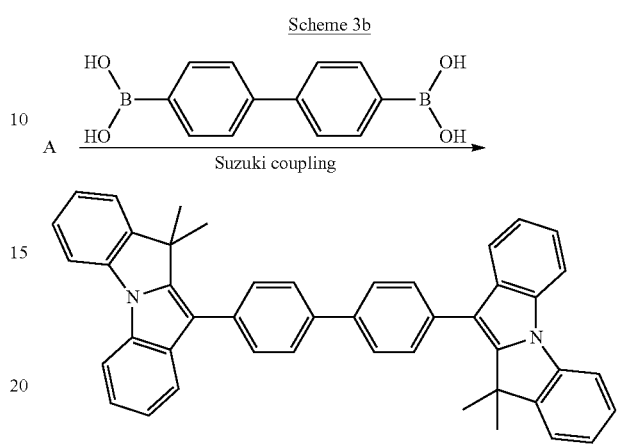

Scheme 3b

Furthermore, other divalent aryl groups can also be employed in the Suzuki coupling in such reactions, for example heteroaryl groups, such as dibenzothiophene, or other aryl groups, such as benzene, fluorene or terphenyl.

Scheme 4a shows by way of example for skeleton A further ways of obtaining compounds of the formula (I) according to the invention by derivatisation reactions. An analogous procedure can be used for skeleton B. The intermediate obtained is a skeleton C.

To this end, firstly a monobromination is carried out in order to obtain the corresponding 5-bromoindole. An aryl group or a diarylamine is subsequently introduced as substituent at position 5 of the indole ring by means of Suzuki reaction or Buchwald reaction.

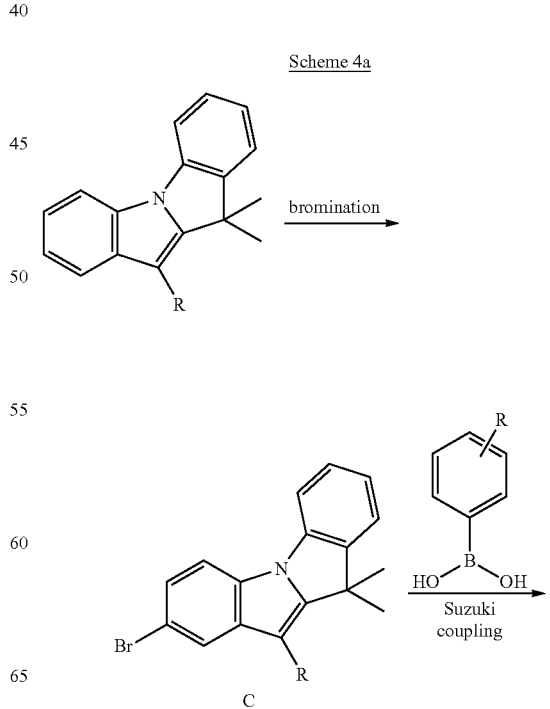

Scheme 4a

C

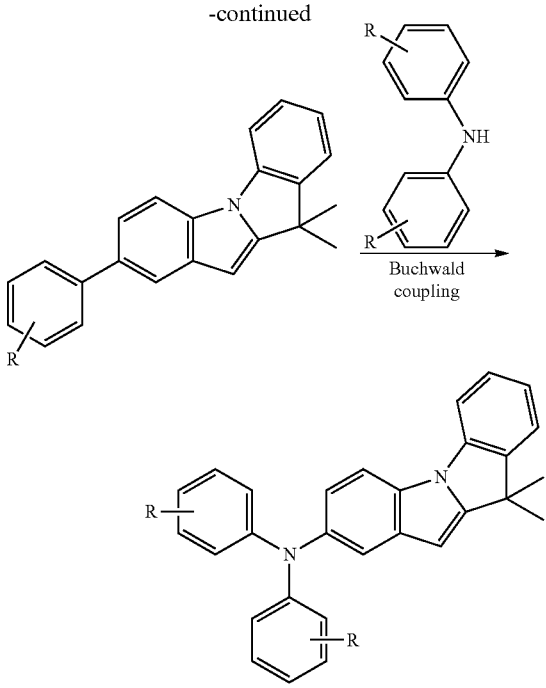

Scheme 4b shows by way of example how compounds of the formula (II) according to the invention can be obtained by an analogous route to Scheme 4a through the use of bifunctional aryl derivatives in the Buchwald coupling. To this end, a bis-diborono-functionalised aryl derivative, shown for the example of 1,3-diboronobenzene, is employed, to which two groups of skeleton C are coupled.

Scheme 4b

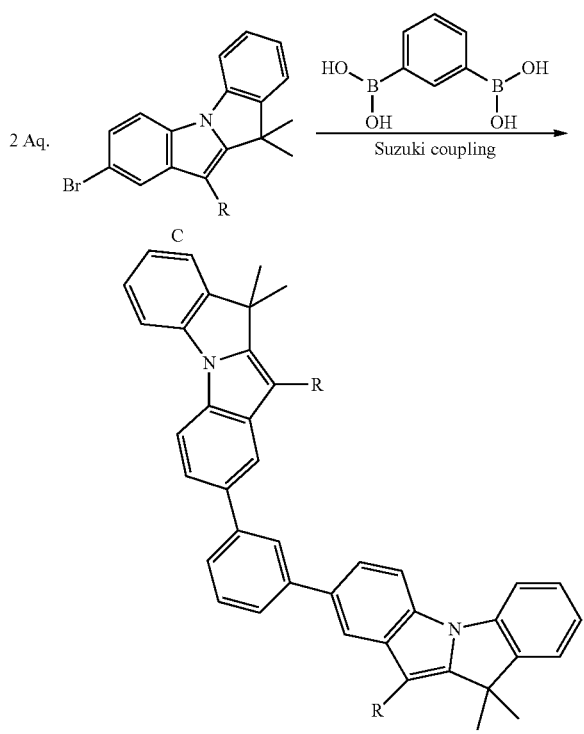

In reactions in accordance with Scheme 4b, compounds of skeleton A can also be employed instead of compounds of skeleton C in order to obtain alternative compounds of the formula (II). Furthermore, other divalent aryl groups can also be employed in the Buchwald coupling in such reactions, for example heteroaryl groups, such as dibenzothiophene, or other aryl groups, such as benzene, fluorene or terphenyl.

The synthetic routes described above are merely intended to serve as examples. The person skilled in the art will be able to fall back on alternative synthetic methods for the synthesis of the compounds according to the invention if it appears advantageous to him under the given circumstances. Furthermore, he will be able to extend and/or modify the syntheses shown using his general expert knowledge in the area of organic synthetic chemistry in order to prepare compounds according to the invention.

The invention thus furthermore relates to a process for the preparation of a compound of the formula (I) or (II) in which the group Q is selected equal to $CR^1$, characterised in that it comprises at least one organometallic coupling reaction between an indole derivative and a halogen-substituted aromatic or heteroaromatic compound and at least one ring-closure reaction between the indole derivative and the coupled aromatic or heteroaromatic compound.

The compounds of the formula (I) or (II) described above, in particular compounds which are substituted by reactive leaving groups, such as bromine, iodine, chlorine, boronic acid or boronic acid ester, can be used as monomers for the preparation of oligomers, dendrimers or polymers. The oligomerisation or polymerisation here preferably takes place via the halogen functionality or the boronic acid functionality.

The invention therefore furthermore relates to oligomers, polymers or dendrimers containing one or more compounds of the formula (I) or (II), where the bond(s) to the polymer, oligomer or dendrimer can be localised at any desired positions in formula (I) or (II) which are substituted by $R^0$ or $R^1$. Depending on the linking of the compound of the formula (I) or (II), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) or (II) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) or (II) may be linked via a trivalent or polyvalent group, for example via a trivalent or polyvalent aromatic or heteroaromatic group, to form a branched or dendritic oligomer or polymer.

The same preferences as described above for compounds of the formula (I) or (II) apply to the recurring units of the formula (I) or (II) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, of which at least one monomer results in recurring units of the formula (I) or (II) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

For the processing of the compounds formula (I) or (II) from liquid phase, for example by spin coating or by printing processes, formulations of the compounds are necessary. These formulations can be, for example, solutions, dispersions or mini-emulsions.

The invention therefore furthermore relates to a formulation, in particular a solution, dispersion or mini-emulsion, comprising at least one compound of the formula (I) or (II) or at least one polymer, oligomer or dendrimer containing at least one unit of the formula (I) or (II) and at least one solvent, preferably an organic solvent. The way in which solutions of this type can be prepared is known to the person skilled in the art and is described, for example, in the applications WO 2002/072714 and WO 2003/019694 and the literature cited therein. Preference is given to a formulation comprising at least one compound of the formula (I) or (II), where the group Q is selected equal to $CR^1$, and at least one solvent.

The compounds of the formula (I) or (II) are suitable for use in electronic devices, in particular in organic electroluminescent devices (OLEDs). Depending on the substitution, the compounds are preferably employed in certain functions and/or layers.

For example, compounds of the formula (I) or (II) which carry at least one group $R^1$-I as substituent $R^1$, as defined above, are particularly suitable for use as matrix material for phosphorescent dopants, as electron-transport material or as hole-blocking material. The group $R^1$-I here preferably contains at least one electron-deficient group, such as six-membered heteroaryl ring groups containing one or more nitrogen atoms or five-membered heteroaryl ring groups containing two or more nitrogen atoms.

Furthermore, compounds of the formula (I) or (II) which carry at least one group $R^1$-II and/or $R^1$-III as substituent $R^1$, as defined above, are particularly suitable for use as hole-transport materials or for use as fluorescent dopants. The group $R^1$-II here preferably contains an aromatic ring system having 12 to 20 aromatic ring atoms.

The compounds of the formula (I) or (II) are preferably employed as electron-transport material in an electron-transport layer, as matrix material in an emitting layer or as hole-transport material in a hole-transport layer. If the compounds are employed as matrix materials in an emitting layer, the emitting layer preferably comprises at least one phosphorescent emitter compound. However, the compounds may also be employed in other layers and/or functions, for example as fluorescent dopants in an emitting layer or as hole- or electron-blocking materials.

The invention therefore furthermore relates to the use of the compounds of the formula (I) or (II) in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention relates, as already mentioned above, to an electronic device comprising anode, cathode and at least one organic layer, where the organic layer comprises at least one compound of the formula (I) or (II). The electronic device here is preferably selected from the above-mentioned devices and is particularly preferably an organic electroluminescent device.

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K.

Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent. The compounds preferably employed in the respective layers and functions are explicitly disclosed in later sections.

It is preferred in accordance with the invention for the compound of the formula (I) or (II) to be employed in an electronic device comprising one or more phosphorescent dopants. The compound can be used in various layers here, preferably in an electron-transport layer, a hole-transport layer, a hole-injection layer or in the emitting layer. However, the compound of the formula (I) or (II) can also be employed in accordance with the invention in an electronic device comprising one or more fluorescent dopants and no phosphorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds according to the invention in organic electroluminescent devices. Further examples of suitable phosphorescent dopants are revealed by the table following in a later section.

In a preferred embodiment of the present invention, the compounds of the formula (I) or (II) are employed as matrix material in combination with one or more dopants, preferably phosphorescent dopants. The compounds are particularly suitable for use as matrix material if they contain one or more groups of the formula $R^1$-I, such as, for example, six-membered heteroaryl ring groups containing one or more nitrogen atoms or five-membered heteroaryl ring groups containing two or more nitrogen atoms.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (I) or (II) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 10/136,109 and WO 2011/000455, or bridged carbazoles, for example in accordance with WO 2011/088877 and WO 2011/128017.

Preferred phosphorescent dopants for use in mixed-matrix systems comprising the compounds according to the invention are the phosphorescent dopants shown in a following table.

In a further preferred embodiment of the invention, the compounds of the formula (I) or (II) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The compounds are used as hole-transport material if, in particular, they are substituted by one or more aromatic ring systems having 12 to 20 aromatic ring atoms and/or by one or more arylamino groups.

If the compound of the formula (I) or (II) is employed as hole-transport material in a hole-transport layer, the compound can be employed as pure material, i.e. in a proportion of 100%, in the hole-transport layer or it can be employed in combination with further compounds in the hole-transport layer.

In a further embodiment of the invention, the compounds of the formula (I) or (II) are employed as fluorescent dopants in an emitting layer. In particular, the compounds are suitable as fluorescent dopants if they are substituted by one or more aromatic systems, preferably aromatic systems containing 12 to 20 aromatic ring atoms. The compounds according to the invention are preferably used as green or blue emitters.

The proportion of the compound of the formula (I) or (II) as dopant in the mixture of the emitting layer is in this case between 0.1 and 50.0% by vol., preferably between 0.5 and 20.0% by vol., particularly preferably between 0.5 and 8.0% by vol. Correspondingly, the proportion of the matrix material is between 50.0 and 99.9% by vol., preferably between 80.0 and 99.5% by vol., particularly preferably between 92.0 and 99.5% by vol.

Preferred matrix materials for use in combination with the compounds according to the invention as fluorescent dopants are mentioned in one of the following sections. They correspond to the matrix materials for fluorescent dopants that are indicated as preferred.

In a further embodiment of the invention, the compounds are employed as electron-transport materials in an electron-transport layer of an organic electroluminescent device. The compounds are particularly suitable for use as electron-transport material if they contain one or more groups of the formula $R^1$-I, such as, for example, six-membered heteroaryl ring groups containing one or more, nitrogen atoms or five-membered heteroaryl ring groups containing two or more nitrogen atoms.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers, where the various colours in this embodiment of the invention together give white light. Particular preference is given to three-layer systems, i.e. systems having three emitting layers, where one or more of these layers comprises a compound of the formula (I) or (II) and where the three layers exhibit blue, green and orange or red emission (for the basic structure see, for example, WO 2005/011013). Likewise, emitters which have broad-band emission bands and thus exhibit white emission are suitable for white emission in such systems. Alternatively and/or additionally, the compounds according to the invention may also be present in a hole-transport layer or electron-transport layer or in another layer in such systems.

The further functional materials preferably employed in the electronic devices comprising one or more compounds of the formula (I) or (II) are shown below.

The compounds shown in the following table are particularly suitable phosphorescent dopants.

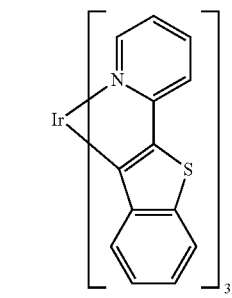

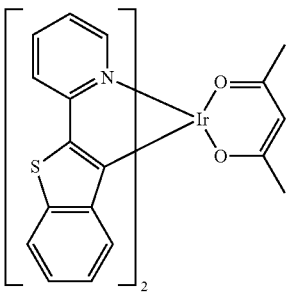

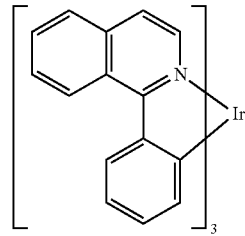

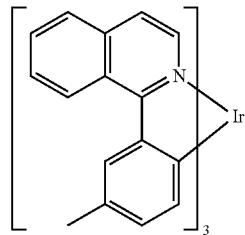

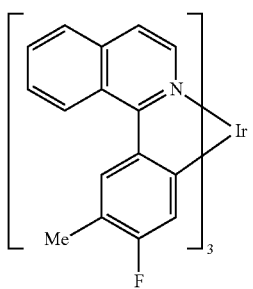
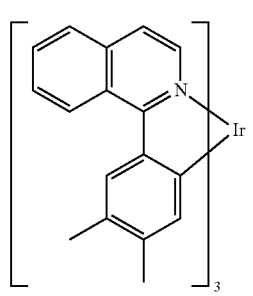
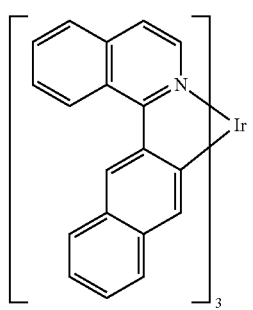
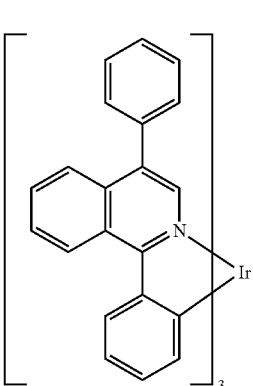
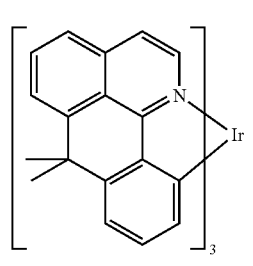
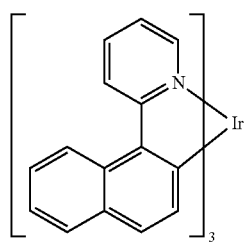
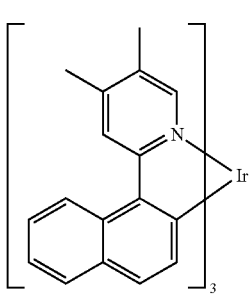
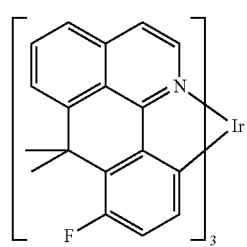
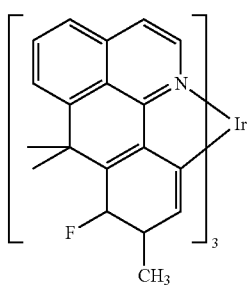
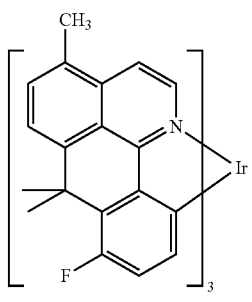

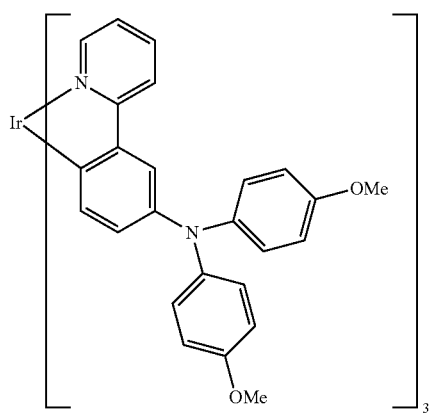
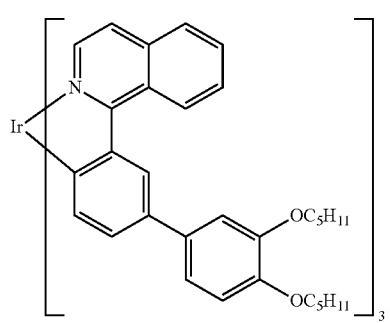
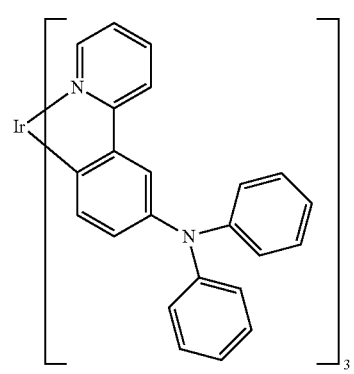
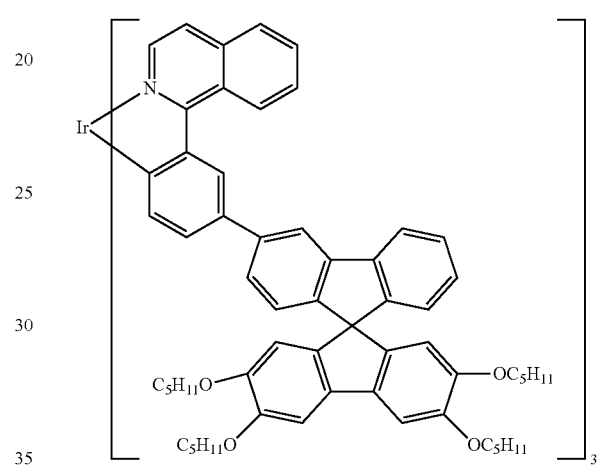
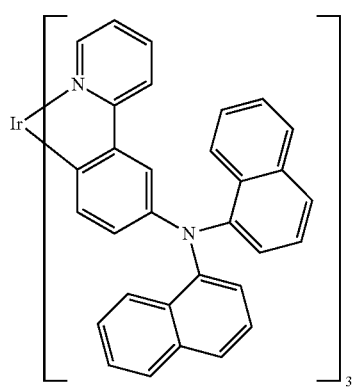
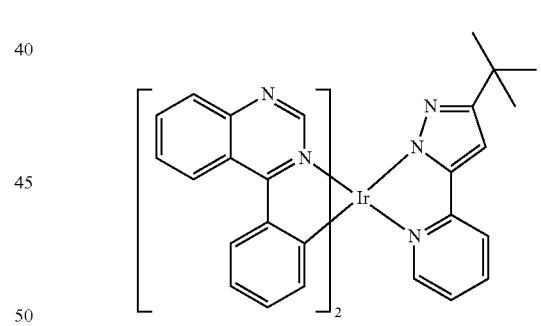
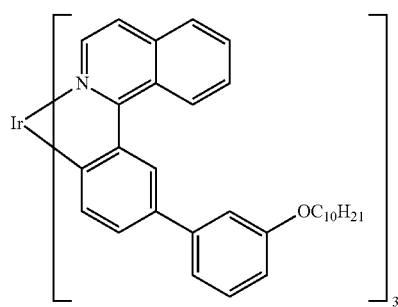
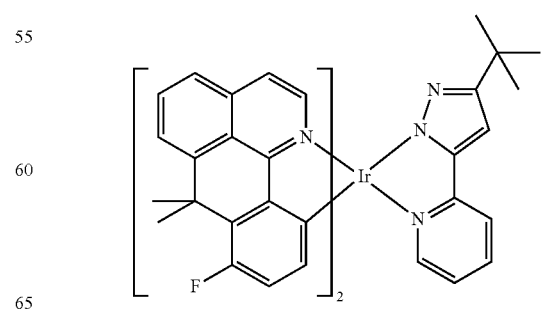

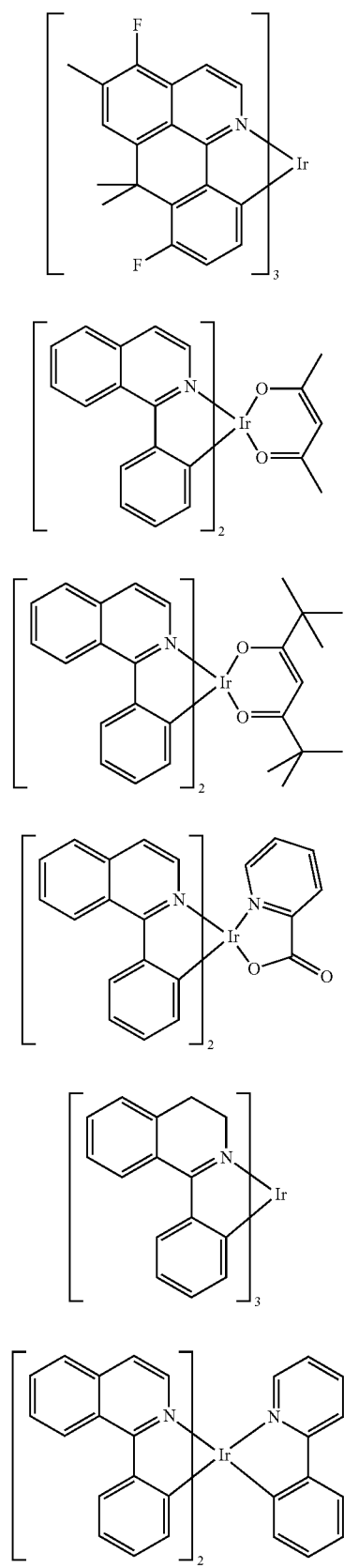
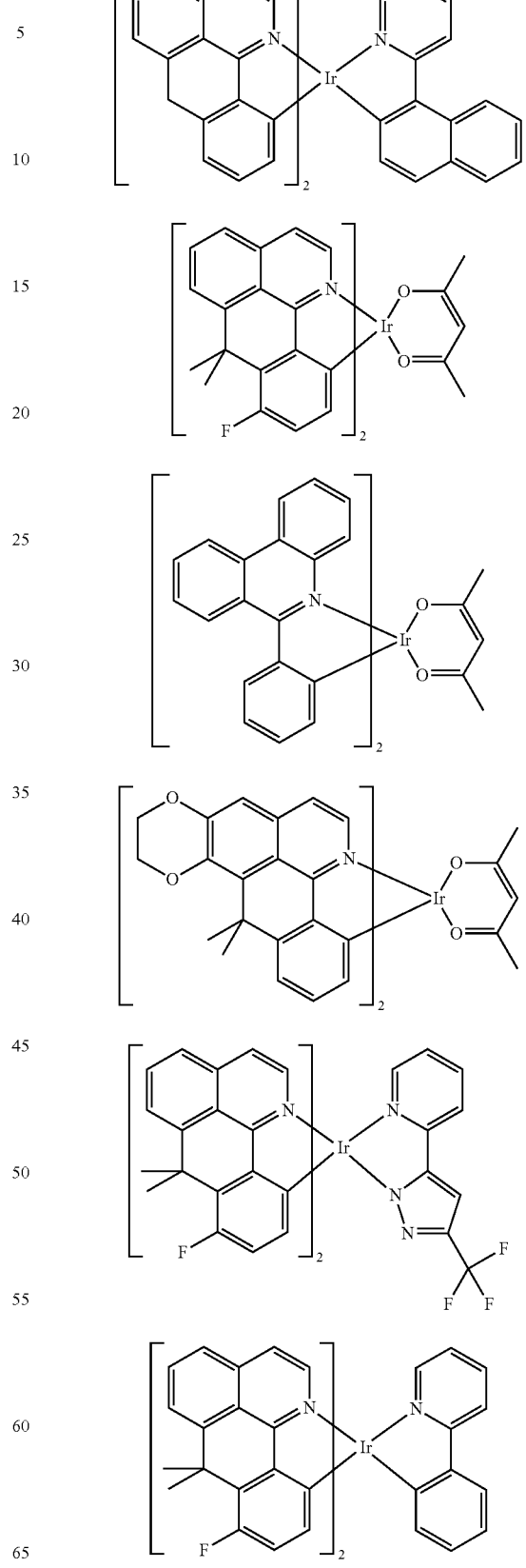

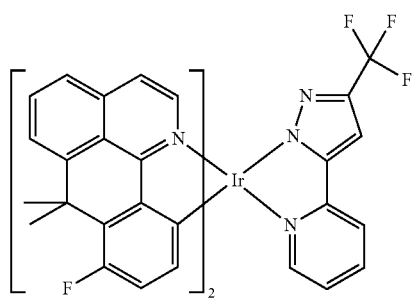
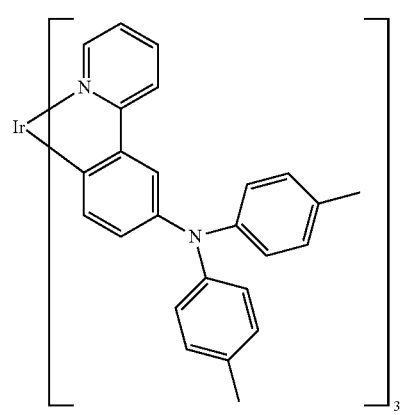
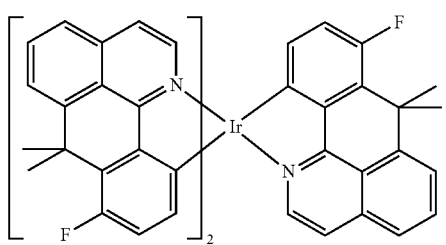
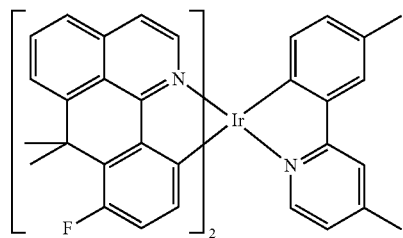
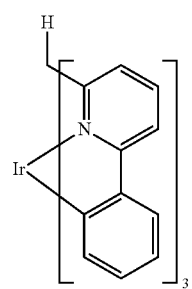
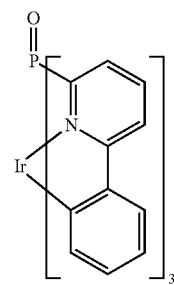
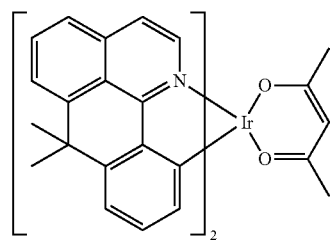
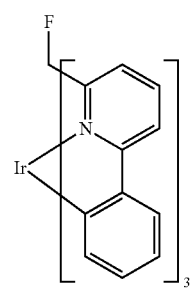
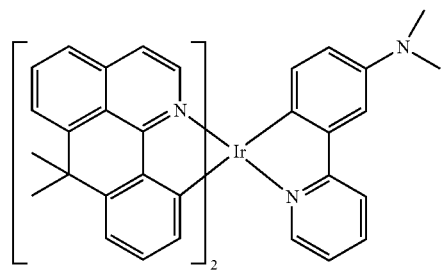
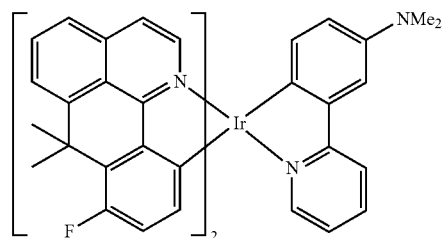
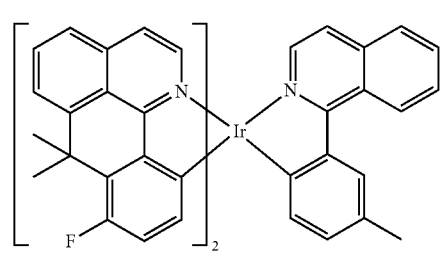

71
-continued
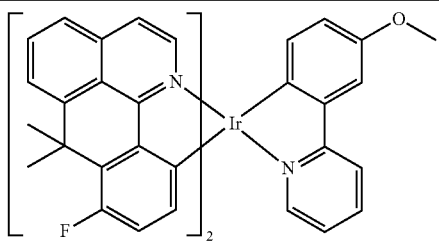
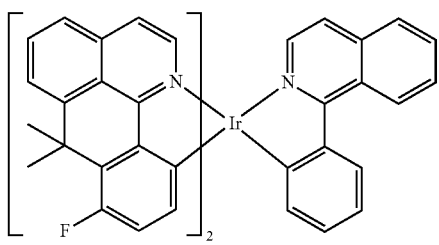
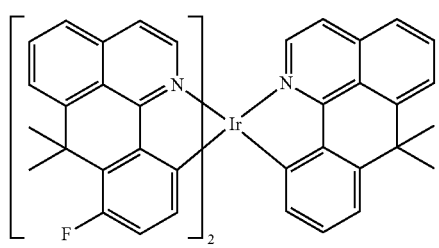
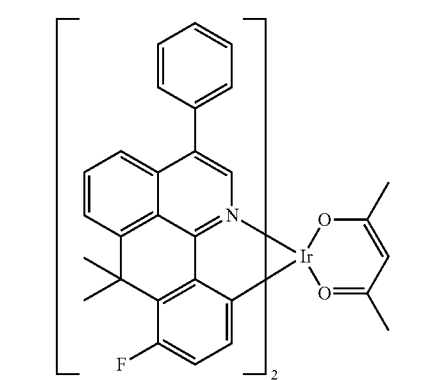
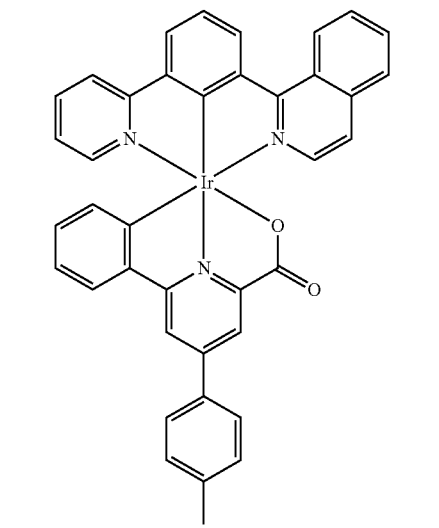
72
-continued
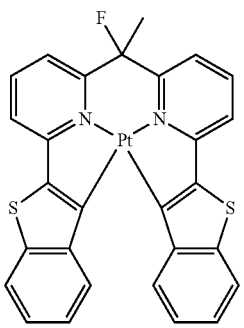
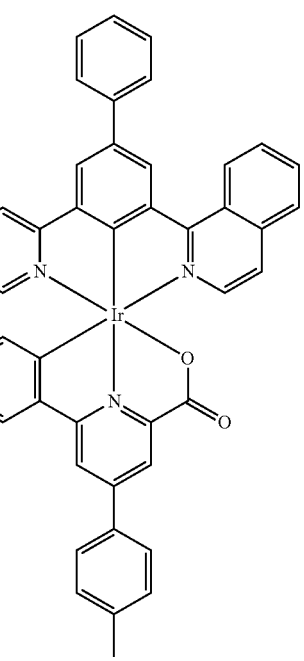
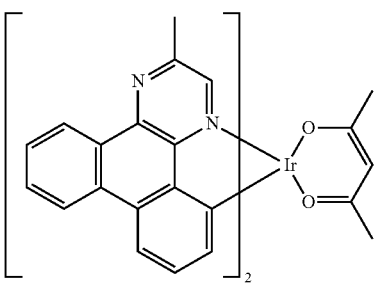
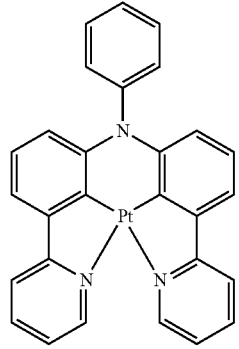

73
-continued
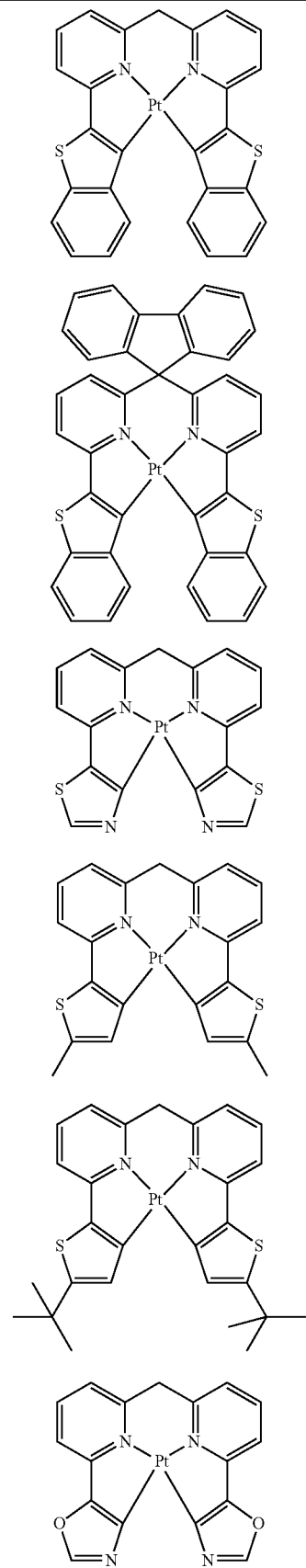
74
-continued
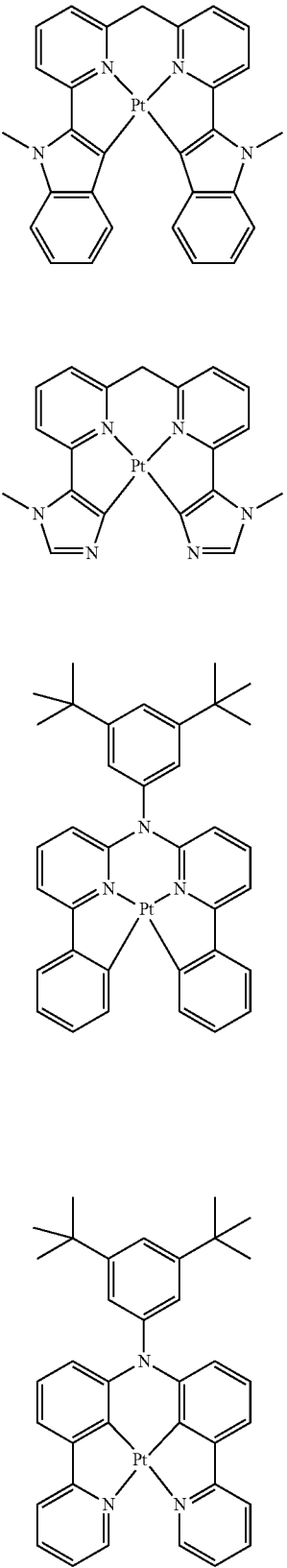

75
-continued
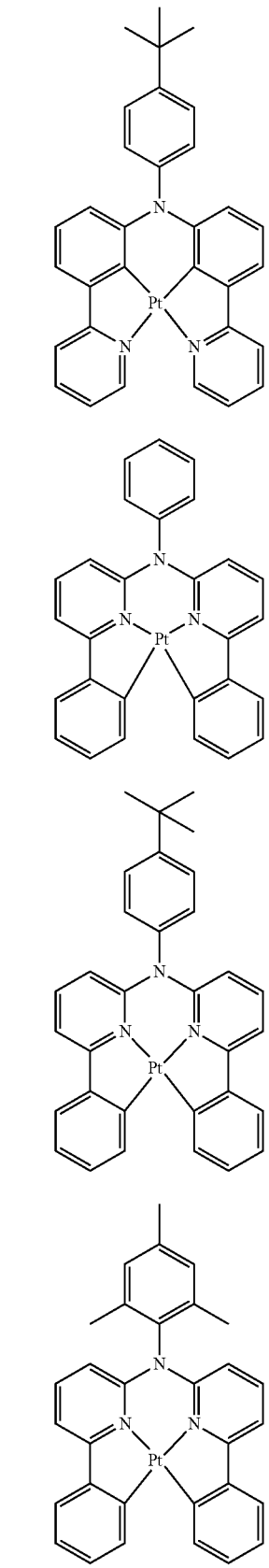
76
-continued
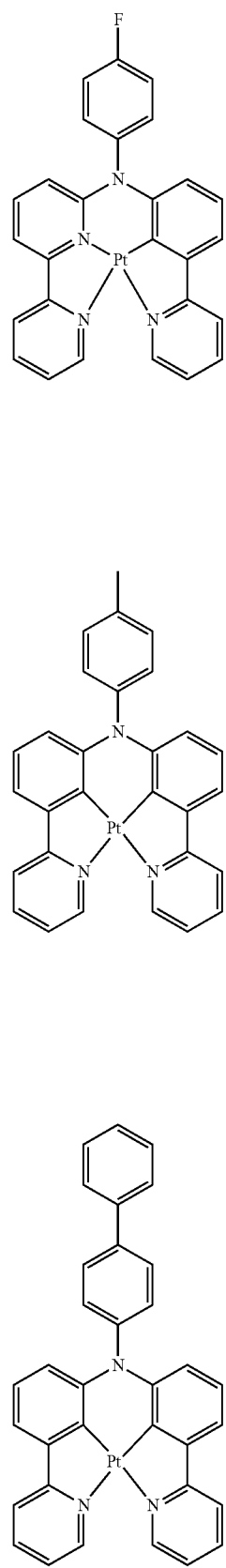

77
-continued
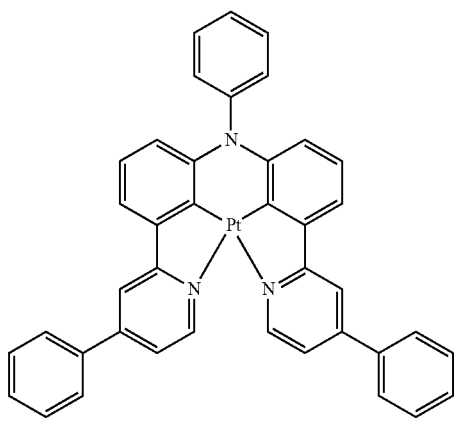
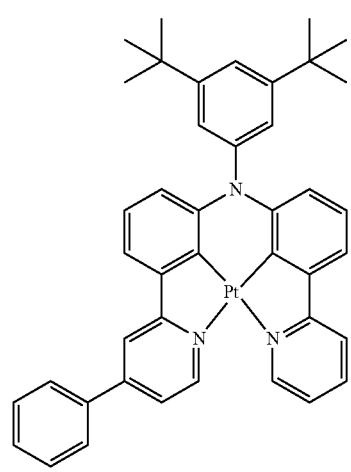
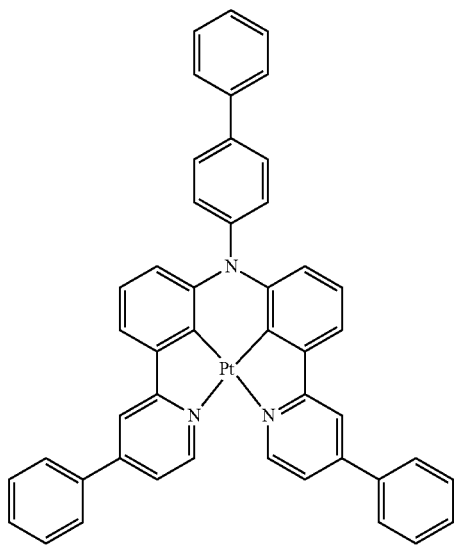
78
-continued
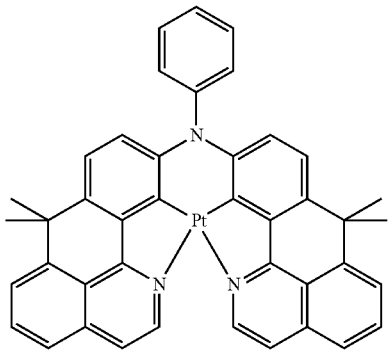
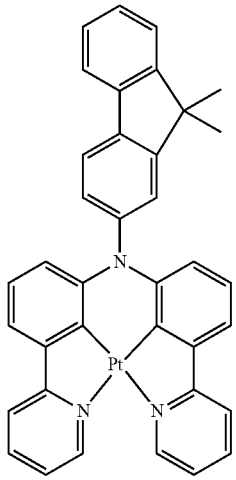
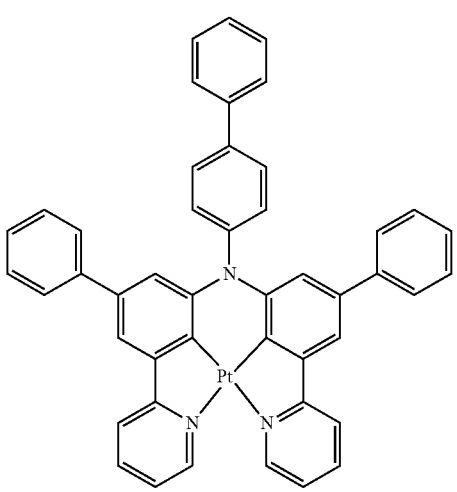

-continued
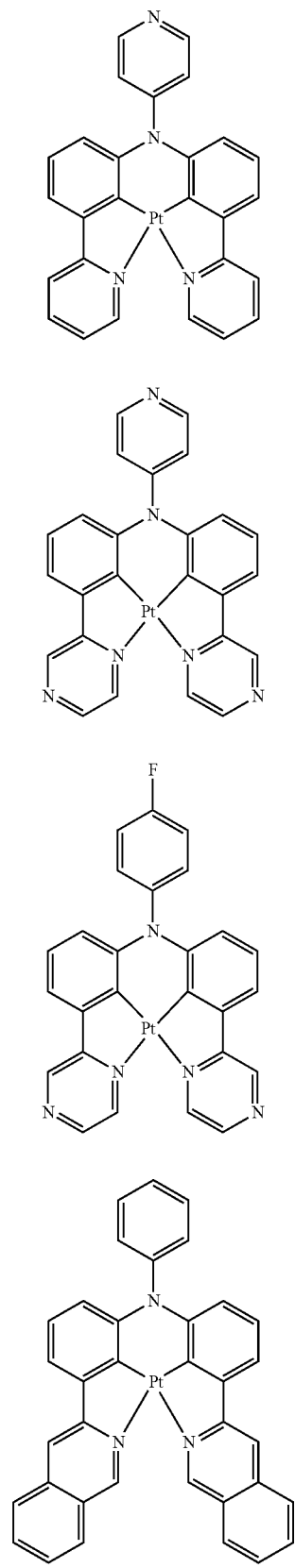
-continued
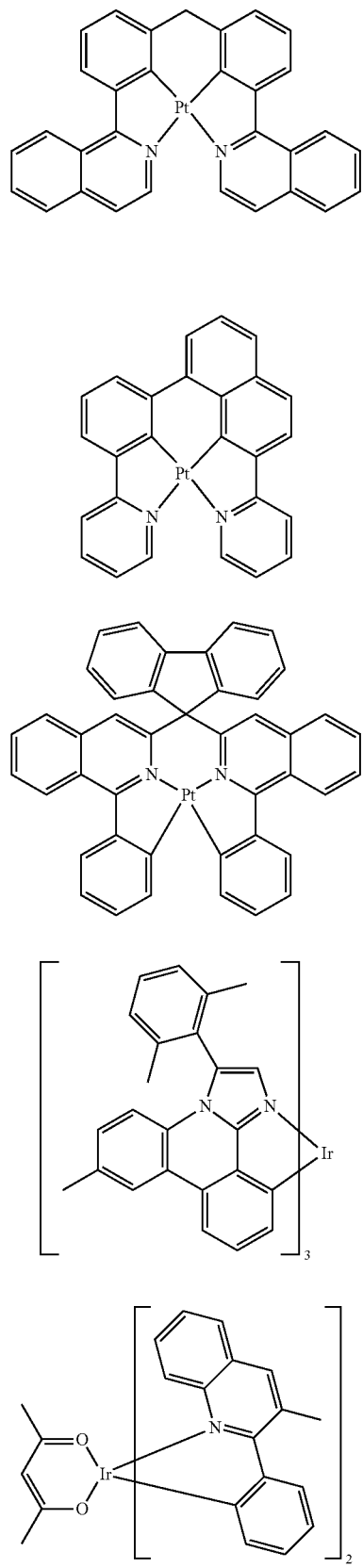

81
-continued
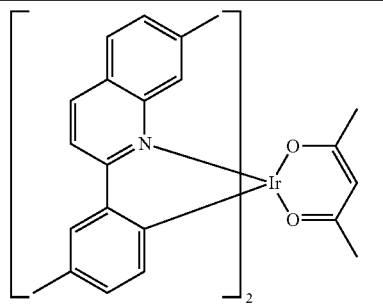
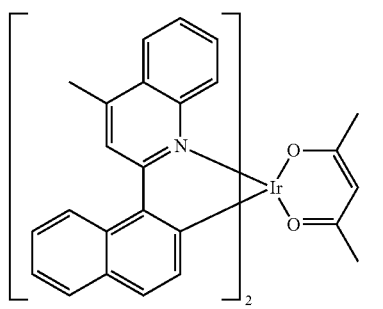
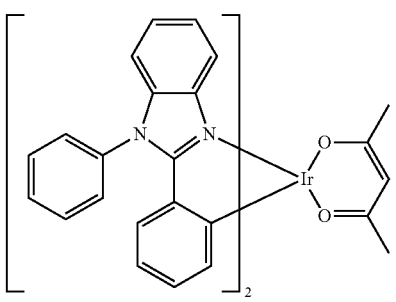
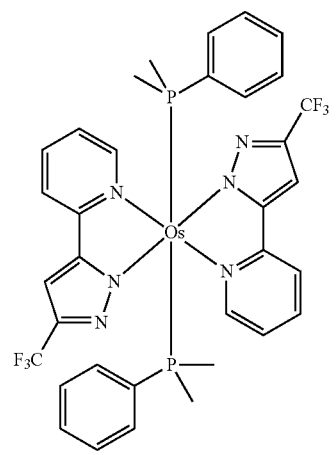
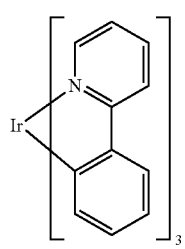
82
-continued
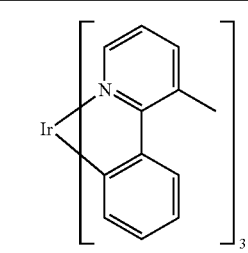
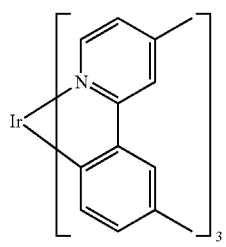
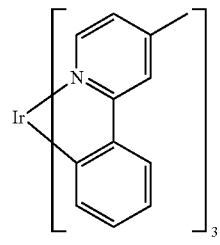
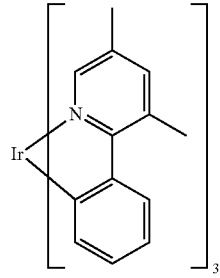
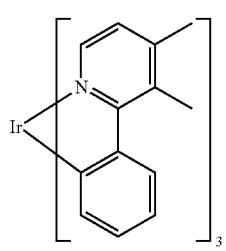
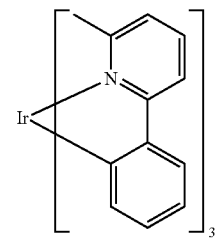

83
-continued
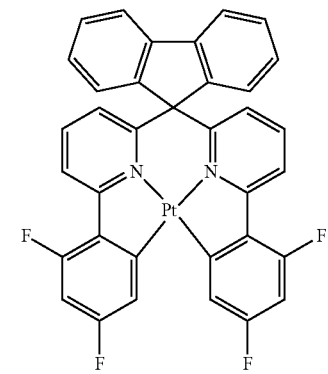
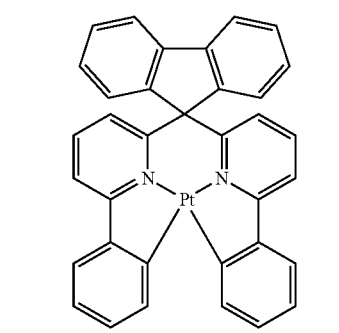
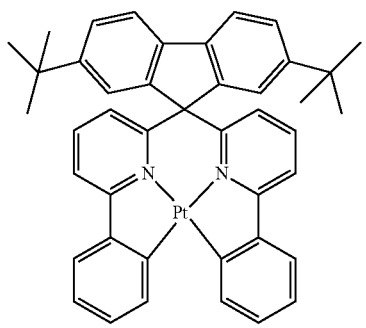
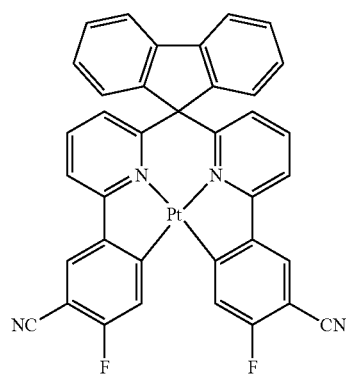
84
-continued
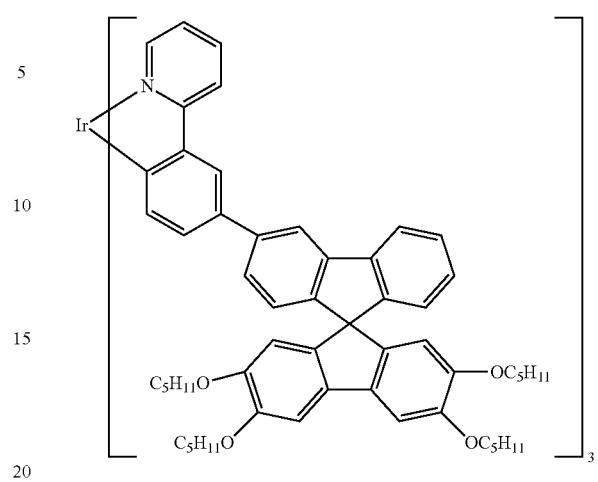

85
-continued
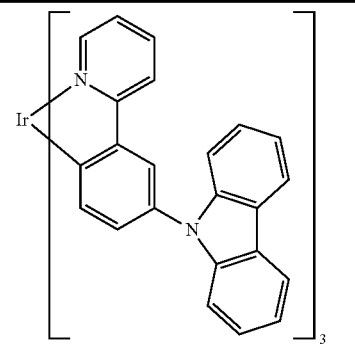
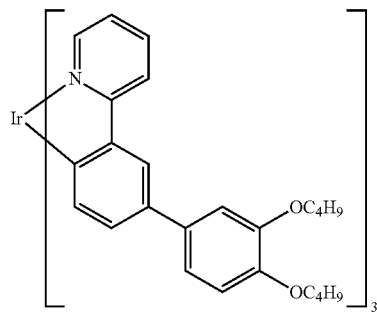
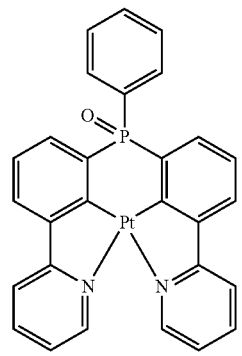
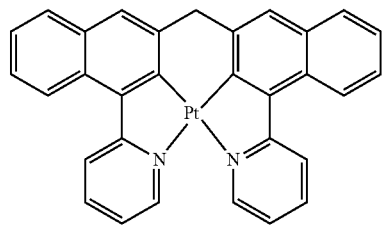
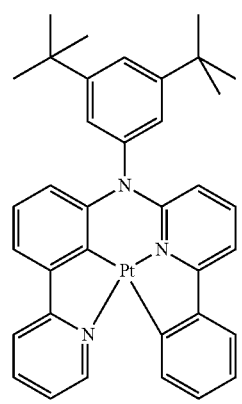
86
-continued
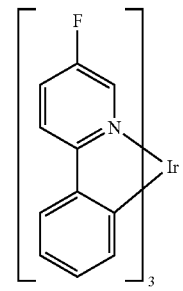
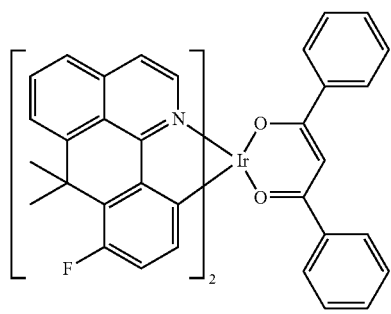
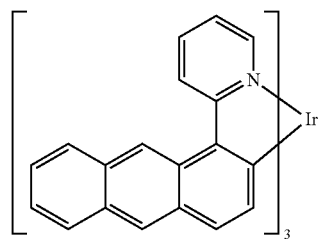
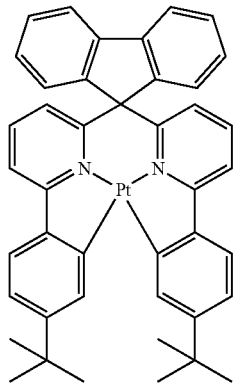
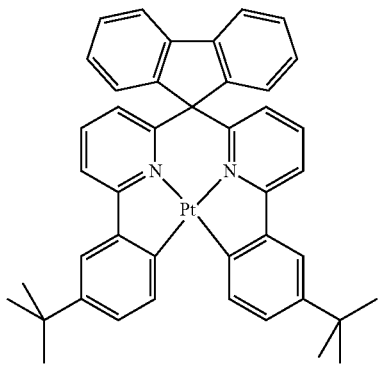

87
-continued
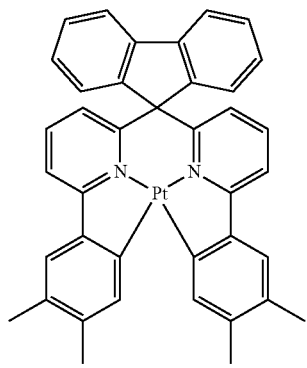
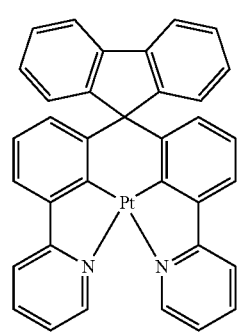
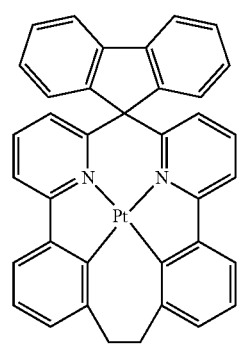
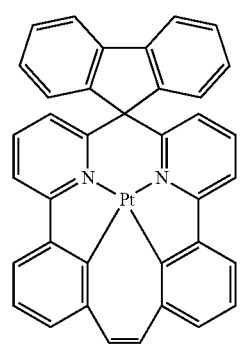
88
-continued
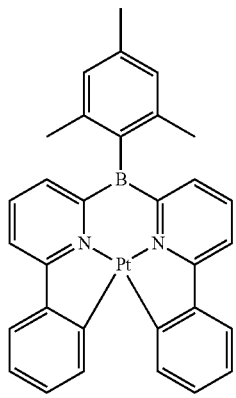
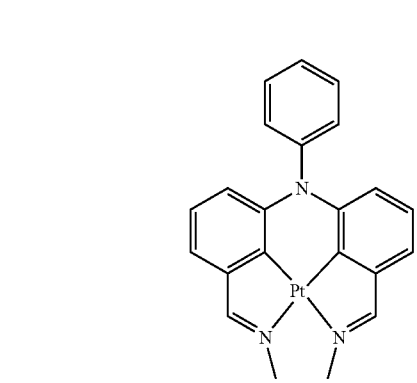
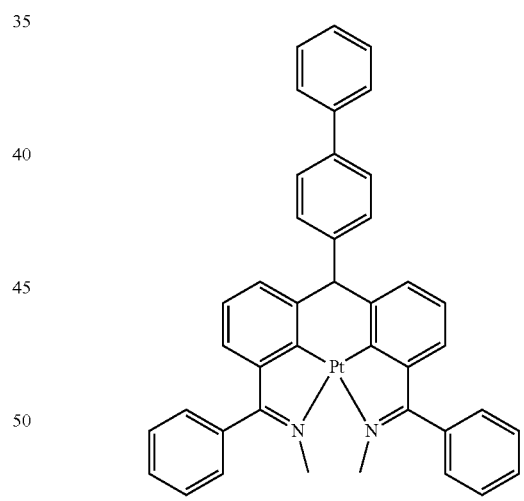
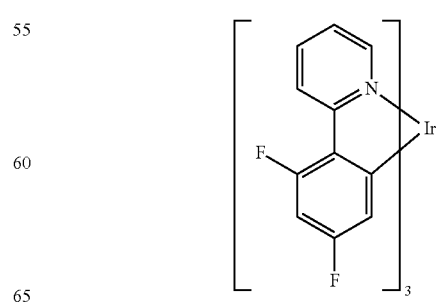

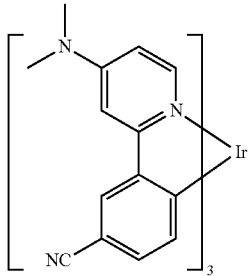
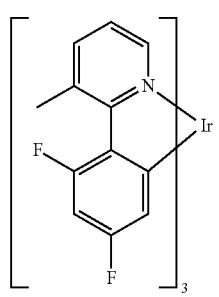
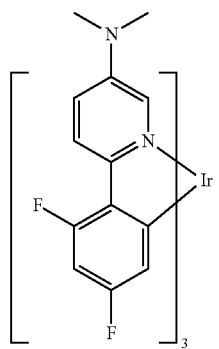
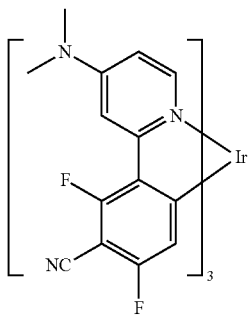
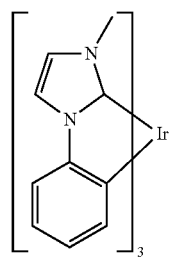
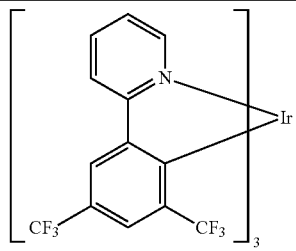
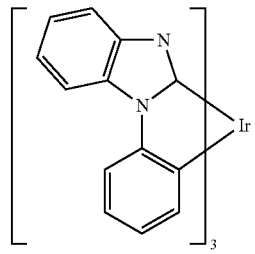
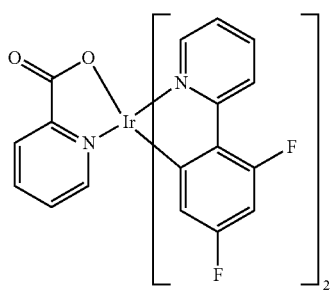
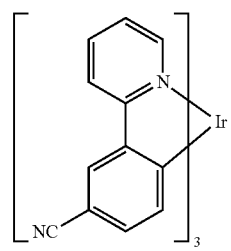
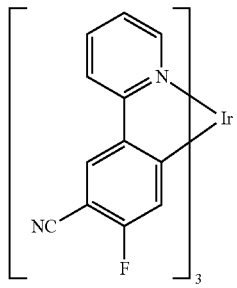

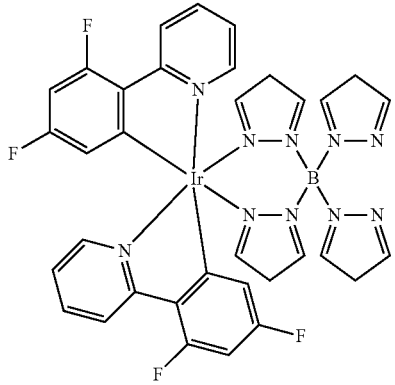

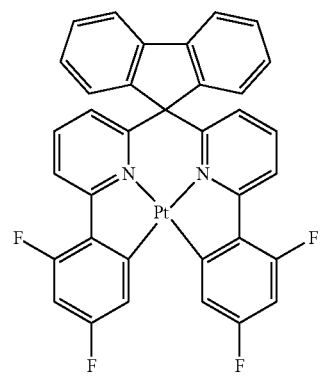

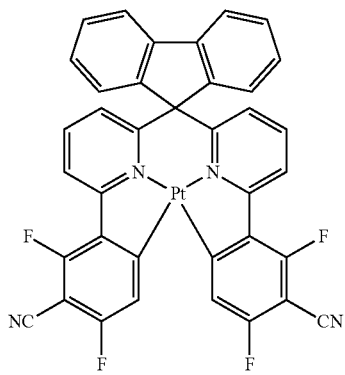

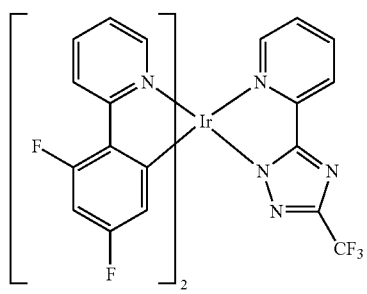

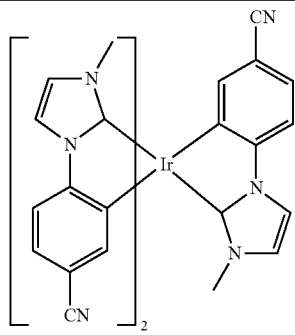

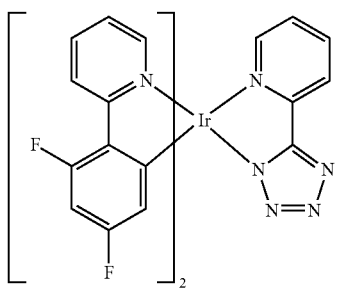

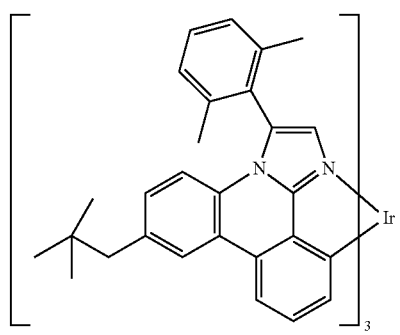

Preferred fluorescent dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding styrylphosphines and styryl ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of fluorescent dopants from the class of the styrylamines are substituted or unsubstituted tristilbenamines or the fluorescent dopants described in WO 2006/000388, WO 2006/058737, WO 2006/000389, WO 2007/065549 and WO 2007/115610. Preference is furthermore given to the condensed hydrocarbons disclosed in WO 2010/012328. Furthermore, the compounds of the formula (I) or (II) can also be used as fluorescent dopants.

Suitable fluorescent dopants are furthermore the structures disclosed in JP 2006/001973, WO 2004/047499, WO 2006/098080, WO 2007/065678, US 2005/0260442 and WO 2004/092111.

Suitable matrix materials, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Preferred matrix materials are furthermore the compounds of the formula (I) or (II). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are disclosed, for example, in WO 2004/018587, WO 2008/006449, U.S. Pat. No. 5,935,721, US 2005/0181232, JP 2000/273056, EP 681019, US 2004/0247937 and US 2005/0211958.

Preferred matrix materials for phosphorescent dopants are carbazole derivatives (for example CBP, N,N-biscarbazolyl-biphenyl) or compounds in accordance with WO 2005/039246, US 2005/0069729, JP 2004/288381, EP 1205527 or WO 2008/086851), triarylamines, azacarbazoles (for example in accordance with EP 1617710, EP 1617711, EP 1731584, JP 2005/347160), indolocarbazole derivatives (for example in accordance with WO 2007/063754 or WO 2008/056746), ketones (for example in accordance with WO 2004/093207 or WO 2010/006680), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), azaboroles or boronic esters (for example in accordance with WO 2006/117052), triazine derivatives (for example in accordance with WO 2010/015306, WO 2007/063754 or WO 2008/056746), zinc complexes (for example in accordance with WO 2009/062578), aluminium complexes (for example BAlq), diazasilole and tetraazasilole derivatives, for example in accordance with WO 2010/054730, indenocarbazole derivatives, for example in accordance with WO 2010/136109 and WO 2011/000455 or diazaphospholes, for example in accordance with WO 2010/054730.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag, Ba/Al or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-6}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) or (II) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds according to the invention can be employed in displays, as light sources in lighting applications and as light sources in medical and/or cosmetic applications (for example light therapy).

On use of the compounds of the formula (I) or (II) in an organic electroluminescent device, one or more of the advantages mentioned below can be achieved:

The compounds according to the invention are very highly suitable for use as matrix materials for phosphorescent dopants and for use as electrontransport materials. On use of the compounds according to the invention in these functions, good power efficiencies, low operating voltages and good lifetimes of the organic electroluminescent devices are obtained.

Furthermore, the compounds according to the invention are distinguished by high oxidation stability in solution, which has an advantageous effect during purification and handling of the compounds and on use thereof in electronic devices.

Furthermore, the compounds according to the invention are temperature-stable and can thus be sublimed substantially without decomposition. Purification of the compounds is thus simplified, and the compounds can be obtained in higher purity, which has a positive effect on the performance data of the electronic devices comprising the materials. In particular, devices having longer operating lifetimes can thus be produced.

The invention is explained in greater detail by the following working examples, with the invention not being restricted to the scope of the examples.

USE EXAMPLES

A) Synthesis Examples

The following syntheses are carried out, unless indicated otherwise, under a protective-gas atmosphere in dried solvents. The solvents and reagents indicated are commercially available.

Example 1: 11-[3-(4,6-Diphenyl-1,3,5-triazin-2-yl)phenyl]-10,10-dimethyl-10H-indolo[1,2-a]indole

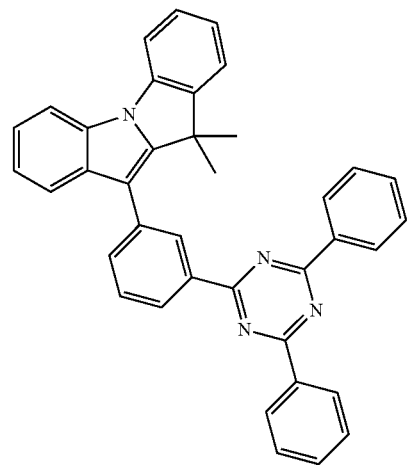 [SMILES: CC1(C)c2ccccc2-n2c1c(-c1cccc(-c3nc(-c4ccccc4)nc(-c4ccccc4)n3)c1)c1ccccc12]

1st Step:
50 g (285 mmol) of 2-methyl indole-2-carboxylate, 116.4 g (571 mmol) of iodobenzene and 98.5 g of $K_2CO_3$ (712.5 mmol) are suspended in 1 l of toluene. 15.8 g (114 mmol) of CuI and 10.06 g of N,N'-dimethylenediamine (114 mmol) are added to this suspension. The reaction mixture is heated under reflux for 48 h. After cooling, the precipitate is filtered off via a fluted filter. The reaction solution is subsequently partitioned between ethyl acetate and water, the organic phase is washed three times with water, dried over $Na_2SO_4$ and evaporated in vacuo. The black-green oil remaining is filtered through silica gel with heptane:toluene. The evaporated filtrate residue is subsequently recrystallised from methanol. Yield: 57 g of 1-phenyl-1H-indole-2-methylcarboxylate (80%)

2nd Step:
57 g (227 mmol) of 1-phenyl-1H-indole-2-methylcarboxylate are initially introduced in 500 ml of dimethylformamide. A solution of 40.4 g (227 mmol) of NBS in 100 ml of dimethylformamide is subsequently added dropwise at 0° C. with exclusion of light, the mixture is allowed to come to RT and is stirred at this temperature for a further 4 h. The mixture is subsequently poured into ice-water. The precipitate is filtered, washed with water and subsequently washed with heptane. The product is washed by stirring with hot heptane and filtered off with suction. Yield: 71.1 g, (95%)

3rd Step:
57.48 g of anhydrous cerium(III) chloride (233 mmol) is initially introduced in 700 ml of dry THF. 70 g (212 mmol) of 1-phenyl-3-bromo-1H-indole-2-methylcarboxylate are metered into this solution in portions, and the mixture is stirred for 1 h. The reaction mixture is cooled, and 212 ml (636 mmol) of methylmagnesium chloride solution (3 mol/l in THF) are added dropwise at 5° C. over the course of 40 min. After one hour, the reaction mixture is carefully poured onto ice and extracted three times with dichloromethane. The combined organic phases are dried over Na$_2$SO$_4$ and evaporated. The residue is recrystallised from toluene. Yield: 65.8 g (94%)

4th Step:

157 g of polyphosphoric acid (1.6 mol) and 104 g of methanesulfonic acid (1.1 mol) are initially introduced in 1 l of CH$_2$Cl$_2$. 65 g (197 mmol) of 2-(3-bromo-1-phenyl-1H-indol-2-yl)propan-2-ol in dichloromethane solution (150 ml) are added dropwise to this solution over the course of 30 min, and the mixture is stirred at 50° C. for 1 h. After this time, the reaction mixture is cooled, carefully poured onto ice and extracted three times with dichloromethane. The combined organic phases are dried over Na$_2$SO$_4$ and evaporated. The residue is recrystallised from toluene. Yield: 52.3 g of 11-bromo-10,10-dimethyl-10H-indolo[1,2-a]indole (85%)

5th Step:

20 g (57 mmol) of 11-bromo-10,10-dimethyl-10H-indolo[1,2-a]indole, 25 g (57 mmol) of 2,4-diphenyl-6-[3-(4,4,5,5-tetramethyl-1,3,2-dioxaborolan-2-yl)phenyl]-1,3,5-triazine and 86 ml of a 2M sodium carbonate solution are suspended in 500 ml of ethylene glycol dimethyl ether. 1.66 g (1.43 mmol) of Pd(PPh$_3$)$_4$ are added to this suspension. The reaction mixture is heated under reflux for 5 h. After cooling, the precipitated solid is filtered off with suction and washed with water and ethanol and dried. The residue is extracted with hot toluene, recrystallised from toluene and finally sublimed in a high vacuum. The purity is 99.9%. Yield: 19.5 g (59%).

Example 2: Bisbiphenyl-4-yl-[4-(11,11-dimethyl-1H-indolo[1,2-a]indol-10-yl)phenyl]amine

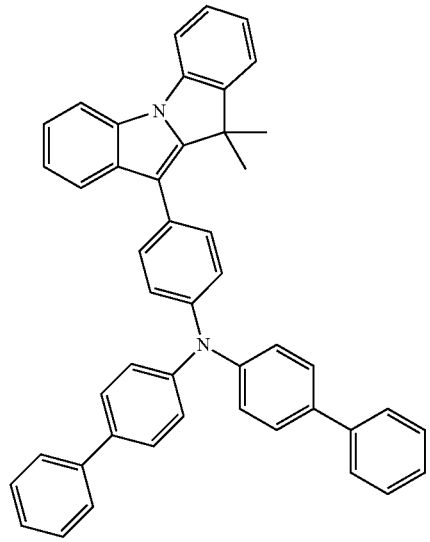 [SMILES: CC1(C)c2ccccc2-n2c1c(-c1ccc(N(c3ccc(-c4ccccc4)cc3)c3ccc(-c4ccccc4)cc3)cc1)c1ccccc12]

20 g (64 mmol) of 11-bromo-10,10-dimethyl-10H-indolo[1,2-a]indole (4th step of Example 1), 33.5 g (64 mmol) of bisbiphenyl-4-yl-[4-(4,4,5,5-tetramethyl-1,3,2-dioxaborolan-2-yl)phenyl]amine and 96 ml of a 2M sodium carbonate solution are suspended in 500 ml of ethylene glycol dimethyl ether. 1.66 g (1.43 mmol) of Pd(PPh$_3$)$_4$ are added to this suspension. The reaction mixture is heated under reflux for 10 h. After cooling, the precipitated solid is filtered off with suction, washed with water and ethanol and dried. The residue is extracted with hot toluene, recrystallised from toluene and subsequently sublimed in a high vacuum. The purity is 99.9%. Yield: 26 g (65%).

Example 3: Bis-10,10'-[(4-4'-biphenyl)-11,11-dimethyl-1H-indolo-[1,2-a]indole

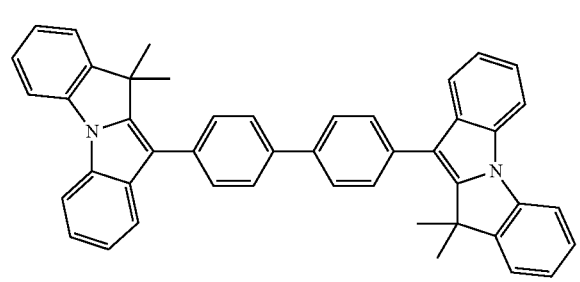 [SMILES: CC1(C)c2ccccc2-n2c1c(-c1ccc(-c3ccc(-c4c5n(c6ccccc46)-c4ccccc4C5(C)C)cc3)cc1)c1ccccc12]

30 g (96 mmol) of 11-bromo-10,10-dimethyl-10H-indolo[1,2-a]indole (4th step of Example 1), 11.6 g (48 mmol) of 4,4'-biphenyldiboronic acid and 145 ml of a 2M sodium carbonate solution are suspended in 600 ml of ethylene glycol dimethyl ether. 2.77 g (2.4 mmol) of Pd(PPh$_3$)$_4$ are added to this suspension. The reaction mixture is heated under reflux for 12 h. After cooling, the precipitated solid is filtered off with suction, washed with water and ethanol and dried. The residue is extracted with hot toluene, recrystallised from toluene and subsequently sublimed in a high vacuum. The purity is 99.9%. Yield: 35.6 g (60%).

Example 4

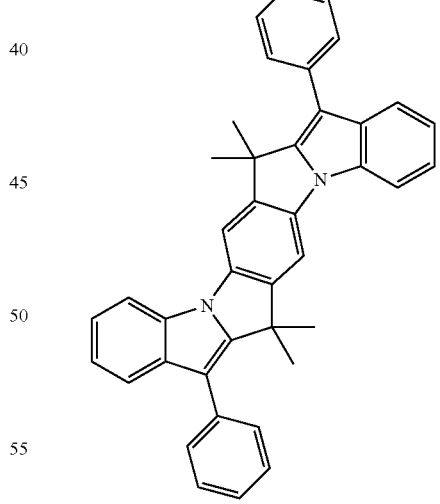

1st Step:

50 g (285 mmol) of 2-methyl indole-2-carboxylate, 47 g (143 mmol) of 1,4-diiodobenzene and 98.5 g of K$_2$CO$_3$ (712.5 mmol) are suspended in 1 l of toluene. 15.8 g (114 mmol) of CuI and 10.06 g of N,N'-dimethylenediamine (114 mmol) are added to this suspension. The reaction mixture is heated under reflux for 48 h. After cooling, the precipitate is filtered off via a fluted filter. The reaction solution is subsequently partitioned between ethyl acetate and water, the organic phase is washed three times with water, dried over Na$_2$SO$_4$ and evaporated in a rotary evaporator. The black-green oil remaining is filtered through silica gel with heptane:toluene. The evaporated filtrate residue is recrystallised from methanol. Yield: 48.5 g of 1,4-di(1H-indole-2-methylcarboxylat-1-yl)benzene (80%).

2nd Step:

45 g (106 mmol) of 1,4-di-(1H-indole-2-methylcarboxylat-1-yl)benzene is initially introduced in 500 ml of dimethylformamide. A solution of 37.5 g (212 mmol) of NBS in 100 ml of dimethylformamide is subsequently added dropwise at 0° C. with exclusion of light, the mixture is allowed to come to RT and is stirred at this temperature for a further 4 h. The mixture is subsequently poured into ice-water. The precipitate is filtered, washed with water and subsequently washed with heptane. The product is washed by stirring with hot heptane and filtered off with suction. Yield: 55.5 g (90%).

3rd Step:

30.9 g of anhydrous cerium(III) chloride (172 mmol) is initially introduced in 700 ml of dry THF. 50 g (85.9 mmol) of 1,4-di(1H-indole-3-bromo-2-methylcarboxylat-1-yl)benzene are metered into this solution in portions, and the mixture is stirred for 1 h. The reaction mixture is cooled, and 200 ml (601 mmol) of methylmagnesium chloride solution (3 mol/l in THF) are added dropwise over the course of 40 min at 5° C. After one hour, the reaction mixture is carefully poured onto ice and extracted three times with dichloromethane. The combined organic phases are dried over Na$_2$SO$_4$ and evaporated. The residue is recrystallised from toluene. Yield: 47 g (95%).

4th Step:

26 g of polyphosphoric acid (270 mmol) and 25.9 g of methanesulfonic acid (270 mmol) are initially introduced in 500 ml of CH$_2$Cl$_2$. 45 g (77.3 mmol) of the compound from step 3 in dichloromethane solution (150 ml) are added dropwise to this solution over the course of 30 min, and the mixture is stirred at 50° C. for 1 h. After this time, the reaction mixture is cooled, carefully poured onto ice and extracted three times with dichloromethane. The combined organic phases are dried over Na$_2$SO$_4$ and evaporated. The residue is recrystallised from toluene. Yield: 39.2 g (90%).

5th Step:

35 g (62 mmol) of the compound from the 4th step, 15 g (124 mmol) of phenylboronic acid and 124 ml of a 2M sodium carbonate solution are suspended in 700 ml of ethylene glycol dimethyl ether. 3.58 g (3.1 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene, recrystallised from toluene and subsequently sublimed in a high vacuum. The purity is 99.9%. Yield: 21.8 g (65%).

B) Device Examples

OLEDs according to the invention are produced by a general process in accordance with WO 2004/058911, which is adapted to the circumstances described here (layer-thickness variation, materials).

The data for various OLEDs are presented in Examples E1 to E9 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), to which the matrix material or materials is (are) admixed by co-evaporation in a certain proportion by volume. An expression such as IC1:3:TEG1 (70%:20%:10%) here means that material IC1 is present in the layer in a proportion by volume of 70%, 3 is present in the layer in a proportion of 20% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics) are determined. The electroluminescence spectra are determined at a luminous density of 1000 cd/m$^2$, and the CIE 1931x and y colour coordinates are calculated therefrom. The expression U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$.

The data of the OLEDs are summarised in Table 2. Depending on the substitution pattern, the materials according to the invention can be employed in different layers and functions. Good to very good values for efficiency and voltage can be achieved here.

According to a preferred embodiment, the compounds are used as matrix materials for red- and for green-phosphorescent emitters (Compound Examples 1, 3 and 4). Device examples in this respect are E1-E4, E7 and E9. E1 and E2 here represent examples in which the compounds according to the invention are employed as the only matrix materials, and E3, E4, E7 and E9 represent examples in which the compounds according to the invention are employed in combination with a further matrix material (mixed-matrix systems).

Furthermore, the compounds according to the invention can advantageously be employed as hole-transport materials, as shown with reference to compound Example 2 in device Examples E5 and E6.

Again furthermore, the compounds according to the invention can be employed as electron-transport materials, as shown with reference to compound Example 1 in device Example E5.

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E1 | — | SpA1 20 nm | — | NPB 20 nm | 1:TER1 (85%:15%) 30 nm | — | Alq$_3$ 20 nm | LiF 1 nm |
| E2 | — | SpA1 70 nm | HATCN 5 nm | BPA1 90 nm | 1:TEG1 (90%:10%) 30 nm | — | ST2:LiQ (50%:50%) 40 nm | — |
| E3 | — | SpA1 70 nm | HATCN 5 nm | BPA1 90 nm | ST1:3:TEG1 (30%:60%:10%) 30 nm | IC1 10 nm | ST2:LiQ (50%:50%) 30 nm | — |
| E4 | — | SpA1 70 nm | HATCN 5 nm | BPA1 90 nm | IC1:3:TEG1 (30%:60%:10%) 30 nm | — | ST2:LiQ (50%:50%) 40 nm | — |
| E5 | HATCN 5 nm | SpA1 140 nm | — | 2 20 nm | M1:D1 (95%:5%) 20 nm | — | ST1:LiQ (50%:50%) 30 nm | — |
| E6 | — | SpA1 70 nm | HATCN 5 nm | 2 90 nm | IC1:TEG1 (90%:10%) 30 nm | ST1 10 nm | ST1:LiQ (50%:50%) 30 nm | — |
| E7 | — | SpA1 20 nm | — | NPB 20 nm | ST1:2:TER1 (70%:15%:15%) 30 nm | Alq$_3$ | LiF 20 nm | 1 nm |
| E8 | — | SpA1 70 nm | HATCN 5 nm | BPA1 90 nm | ST1:TEG1 (90%:10%) 30 nm | — | 1 40 nm | LiQ 3 nm |
| E9 | — | SpA1 70 nm | HATCN 5 nm | BPA1 90 nm | IC1:4:TEG1 (70%:20%:10%) 30 nm | IC1 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y |
|---|---|---|---|---|---|
| E1 | 4.7 | 7.7 | 5.1 | 12.8% | 0.69/0.31 |
| E2 | 3.7 | 51 | 43 | 14.1% | 0.36/0.60 |
| E3 | 3.6 | 53 | 46 | 14.8% | 0.36/0.60 |
| E4 | 3.8 | 50 | 41 | 13.9% | 0.36/0.60 |
| E5 | 4.2 | 7.5 | 5.6 | 6.1% | 0.14/0.15 |
| E6 | 3.5 | 55 | 50 | 15.3% | 0.36/0.60 |
| E7 | 4.7 | 6.5 | 4.3 | 10.8% | 0.39/0.61 |
| E8 | 4.3 | 48 | 35 | 13.2% | 0.36/0.60 |
| E9 | 3.5 | 56 | 50 | 15.6% | 0.37/0.61 |

TABLE 3

Structural formulae of the materials for the OLEDs

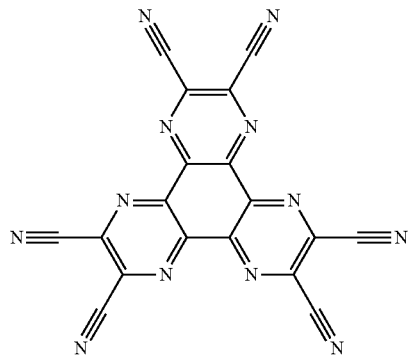 [SMILES: N#Cc1nc2c3nc(C#N)c(C#N)nc3c3nc(C#N)c(C#N)nc3c2nc1C#N]

HATCN

TABLE 3-continued
Structural formulae of the materials for the OLEDs
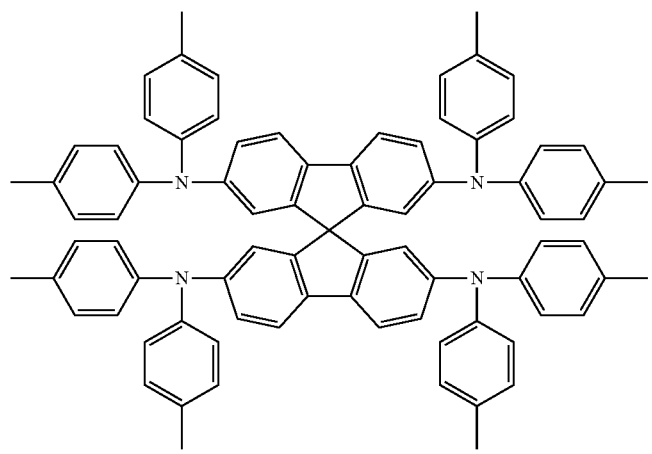
SpA1
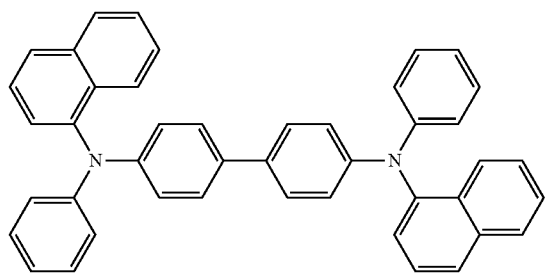 [SMILES: c1ccc(N(c2ccc(-c3ccc(N(c4ccccc4)c4cccc5ccccc45)cc3)cc2)c2cccc3ccccc23)cc1]
NPB
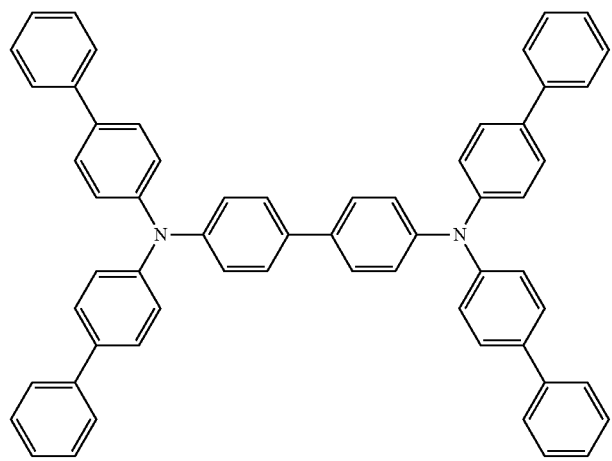 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1
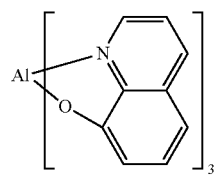
Alq$_3$ TABLE 3-continued
Structural formulae of the materials for the OLEDs
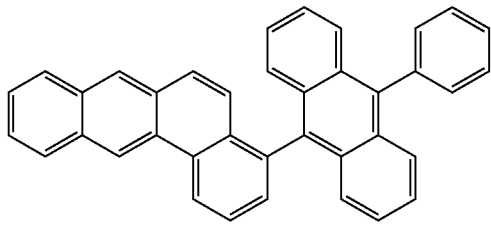 [SMILES: c1ccc(-c2c3ccccc3c(-c3cccc4c3ccc3cc5ccccc5cc34)c3ccccc23)cc1]
M1
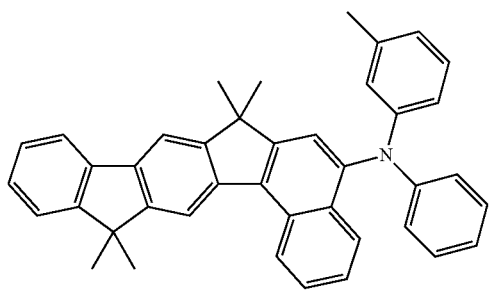 [SMILES: Cc1cccc(N(c2ccccc2)c2cc3c(c4ccccc24)-c2cc4c(cc2C3(C)C)-c2ccccc2C4(C)C)c1]
D1
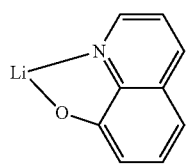
LiQ
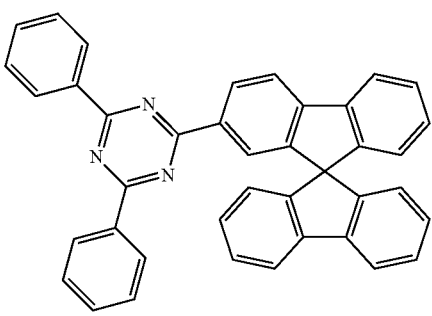 [SMILES: c1ccc(-c2nc(-c3ccccc3)nc(-c3ccc4c(c3)C3(c5ccccc5-c5ccccc53)c3ccccc3-4)n2)cc1]
ST1

TABLE 3-continued
Structural formulae of the materials for the OLEDs
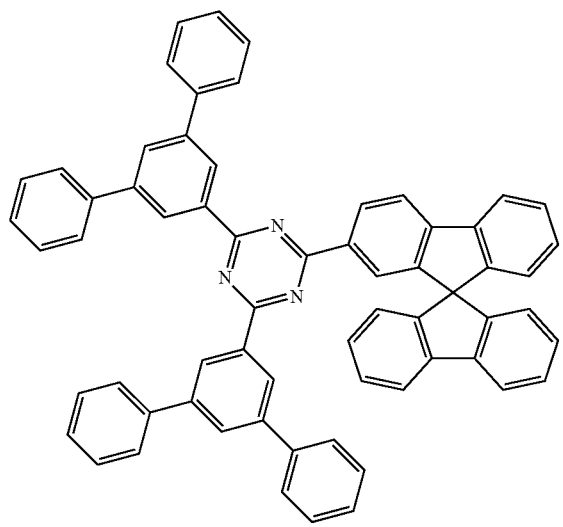 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
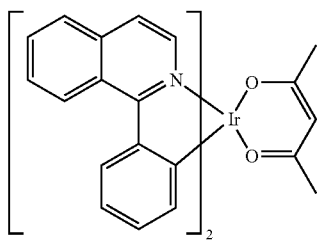
TER1
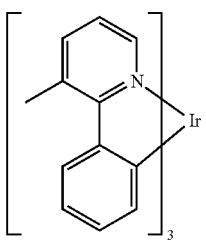
TEG1
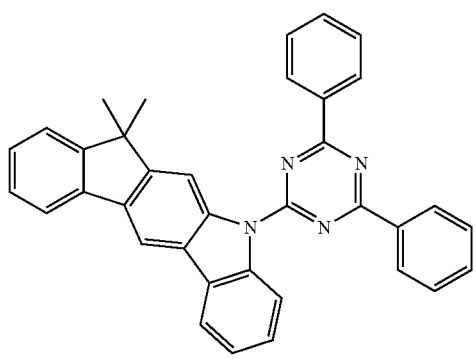 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materials for the OLEDs
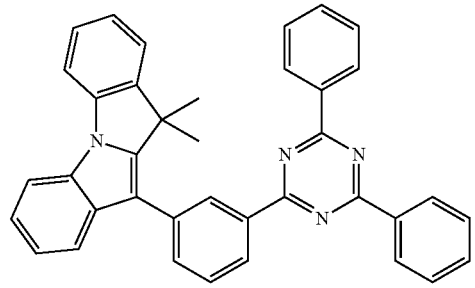 [SMILES: CC1(C)c2ccccc2-n2c1c(-c1cccc(-c3nc(-c4ccccc4)nc(-c4ccccc4)n3)c1)c1ccccc12]
1
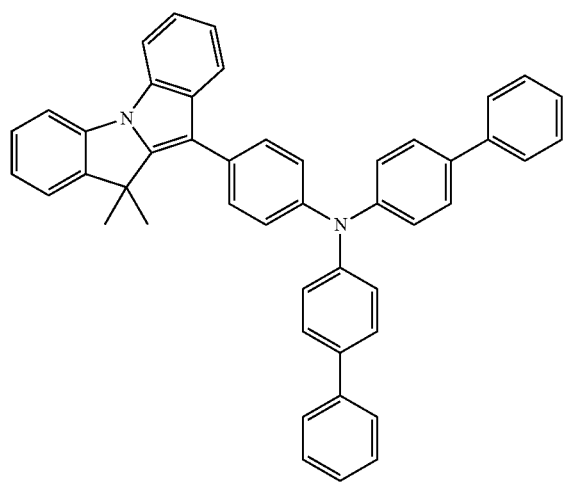 [SMILES: CC1(C)c2ccccc2-n2c1c(-c1ccc(N(c3ccc(-c4ccccc4)cc3)c3ccc(-c4ccccc4)cc3)cc1)c1ccccc12]
2
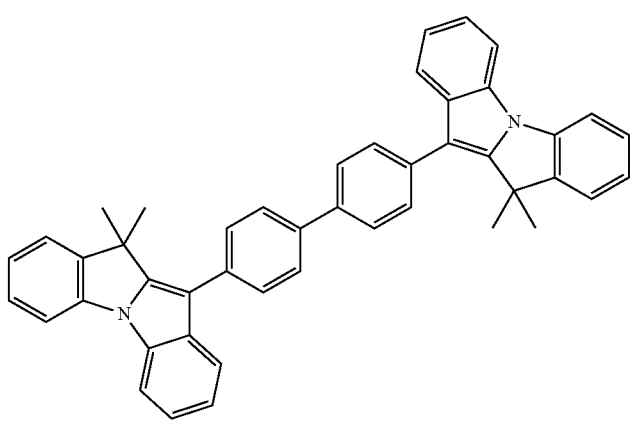 [SMILES: CC1(C)c2ccccc2-n2c1c(-c1ccc(-c3ccc(-c4c5n(c6ccccc46)-c4ccccc4C5(C)C)cc3)cc1)c1ccccc12]
3
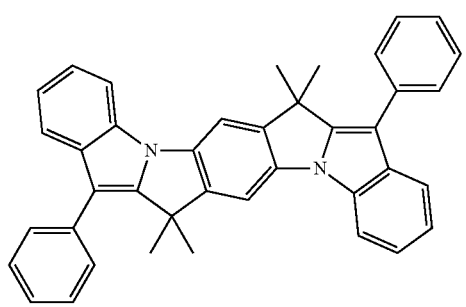 [SMILES: CC1(C)c2cc3c(cc2-n2c1c(-c1ccccc1)c1ccccc12)C(C)(C)c1c(-c2ccccc2)c2ccccc2n1-3]
4

The invention claimed is:
1. An electronic device, comprising an anode, a cathode and at least one organic layer, wherein the organic layer comprises at least one compound of the formula (I) or (II)

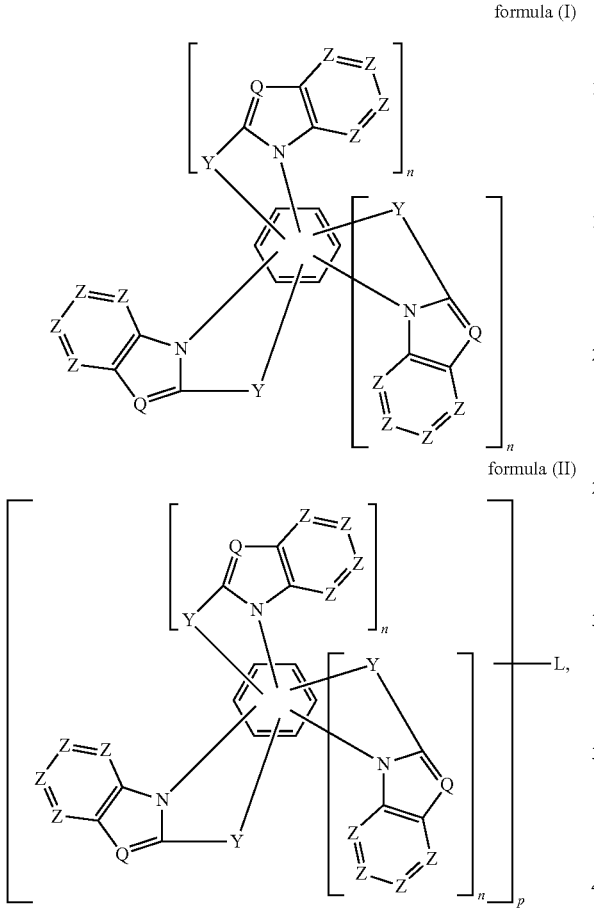

formula (I)

formula (II)

wherein:
Y is C(R$^1$)$_2$;
Z are on each occurrence, identically or differently, CR$^1$ or N;
Q is CR$^1$;
L is selected from C=O, C=NR$^1$, Si(R$^1$)$_2$, NR$^1$, P(=O)(R$^1$), O, S, SO, SO$_2$, alkylene groups having 1 to 20 C atoms or alkenylene or alkynylene groups having 2 to 20 C atoms, where one or more CH$_2$ groups in the said groups may be replaced by Si(R$^1$)$_2$, O, S, C=O, C=NR$^1$, C(=O)O, (C=O)NR$^1$, NR$^1$, P(=O)(R$^1$), SO or SO$_2$ and where one or more H atoms in the said groups may be replaced by D, F, Cl, Br, I, CN or NO$_2$, and aromatic or heteroaromatic ring systems having 5 to 60 aromatic ring atoms, which may in each case be substituted by one or more radicals R$^1$, and any desired combinations of 1, 2, 3, 4 or 5 identical or different groups selected from the above-mentioned groups; or L is a single bond, where p in this case is equal to 2;
R$^1$ is on each occurrence, identically or differently, H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^2$ and where one or more CH$_2$ groups in the above-mentioned groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy, heteroaryloxy, aralkyl or heteroaralkyl group having 5 to 60 aromatic ring atoms, which may be substituted by one or more radicals R$^2$;
R$^2$ is on each occurrence, identically or differently, H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, Ge(R$^3$)$_2$, Sn(R$^3$)$_2$, C=O, C=S, C=Se, C=NR$^3$, —C(=O)O—, —C(=O)NR$^3$—, NR$^3$, P(=O)(R$^3$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy, heteroaryloxy, aralkyl or heteroaralkyl group having 5 to 60 aromatic ring atoms, which may be substituted by one or more radicals R$^3$, where two or more radicals R$^2$ may be linked to one another and may form a ring or a ring system;
R$^3$ is on each occurrence, identically or differently, H, D, F or an aliphatic, aromatic and/or heteroaromatic organic radical having 1 to 20 C atoms, in which, in addition, one or more H atoms may be replaced by D or F; two or more substituents R$^3$ here may also be linked to one another and form a ring or a ring system;
n is on each occurrence, identically or differently, 0 or 1, where, in the case n=0, the group in brackets is not present and optionally groups R$^1$ are instead bonded to the central benzene ring;
p is equal to 2, 3, 4, 5 or 6; and
where the group Y and the nitrogen atom at any desired adjacent positions may be bonded to the aromatic six-membered ring;
where, in the formulae (I) and (II), in each case no or 1, 2 or 3 carbon atoms which are constituents of the central aromatic six-membered ring may be replaced by N if the sum of the indices n is equal to 0, and where, in the formulae (I) and (II), in each case no or 1 or 2 carbon atoms which are constituents of the central aromatic six-membered ring may be replaced by N if the sum of the indices n is equal to 1, and
where, in formula (II), the moieties in square brackets with index p which are bonded to L may be identical or different; and where, in formula (II), the group L may be bonded at any desired position of the moiety in square brackets with index p.

2. The electronic device according to claim 1, wherein p is equal to 2.

3. The electronic device according to claim 1, wherein the sum of the values for n in formula (I) and the sum of the values for n per unit in square brackets with index p in formula (II) is equal to 0.

4. The electronic device according to claim 1, wherein 0 or 1 group Z per aromatic ring is equal to N.

5. The electronic device according to claim 1, wherein L is selected from a single bond, where in this case p=2, or from C=O, $NR^1$, O or S, where in these cases p=2, or from alkylene groups having 1 to 10 C atoms, alkenylene groups having 2 to 10 C atoms, where one or more $CH_2$ groups in the said groups may be replaced by C=O, $NR^1$, $P(=O)(R^1)$, O or S, and arylene or heteroarylene groups having 5 to 20 aromatic ring atoms, which may be substituted by one or more radicals $R^1$, or from divalent aromatic or heteroaromatic ring systems of the formula (L-1)

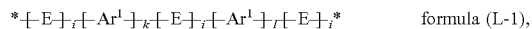
formula (L-1), where p in this case is equal to 2 and wherein:

$Ar^1$ is on each occurrence, identically or differently, an aryl or heteroaryl group having 5 to 20 aromatic ring atoms, which may in each case be substituted by one or more radicals $R^1$;

E is on each occurrence, identically or differently, a single bond, C=O, $NAr^1$, $P(=O)(R^1)$, O, S, SO or $SO_2$;

i is on each occurrence, identically or differently, 0 or 1;

k,l are on each occurrence, identically or differently, 0, 1, 2 or 3, where the sum of the values of k and l is greater than 0; and where the groups $Ar^1$ may be connected to one another via one or more divalent groups T, where T is selected on each occurrence, identically or differently, from a single bond, $BR^1$, $C(R^1)_2$, C=O, C=S, C=$NR^1$, C=$C(R^1)_2$, $CR^1$=$CR^1$, $Si(R^1)_2$, $NR^1$, $PR^1$, $P(=O)R^1$, O, S, S=O and $S(=O)_2$; and the symbols * mark bonds from the group L to the remainder of the compound.

6. The electronic device according to claim 1, wherein the compound of the formula (I) is selected from the formulae

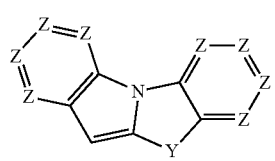
formula (I-1)

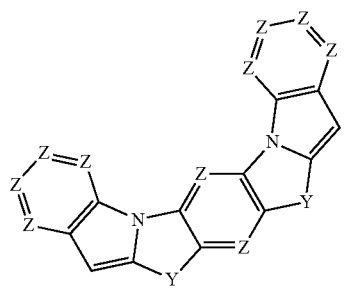
formula (I-2)

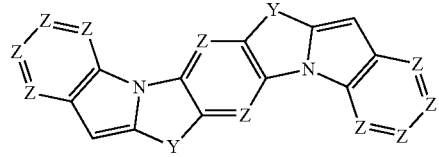
formula (I-3)

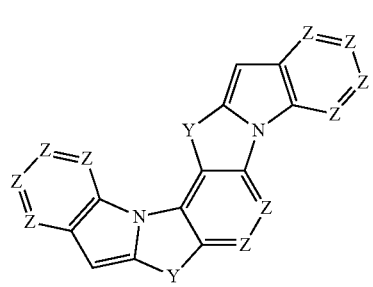
formula (I-4)

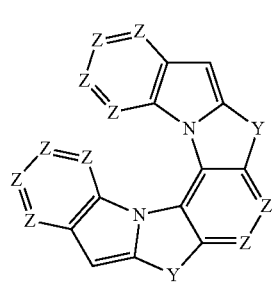
formula (I-5)

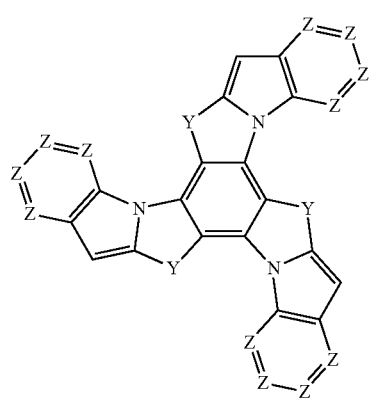
formula (I-6)

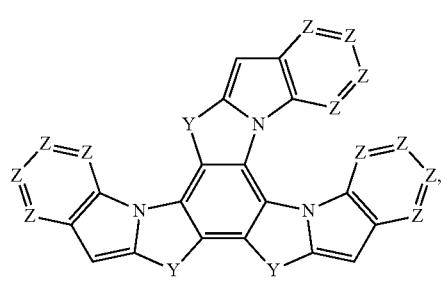
formula (I-7)

where the compounds may be substituted by radicals $R^1$ at all unsubstituted positions.

7. The electronic device according to claim 1, wherein the compound of the formula (II) is selected from the formulae formula (II-A-1)
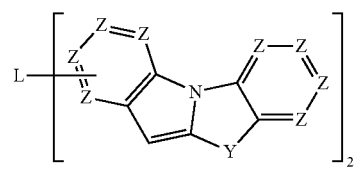
formula (II-A-2)
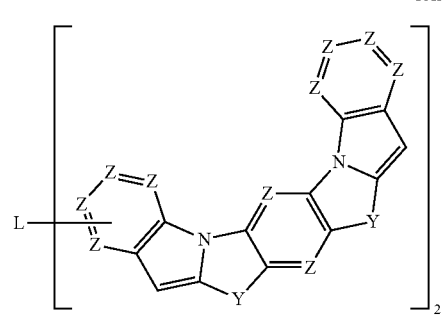
formula (II-A-3)
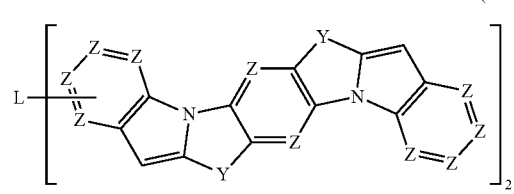
formula (II-A-4)
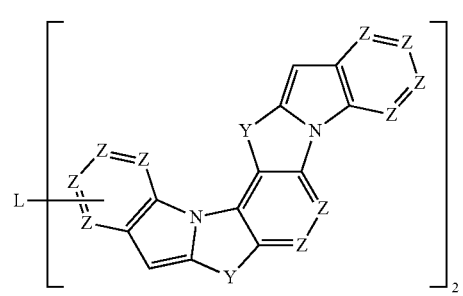
formula (II-A-5)
formula (II-A-6)
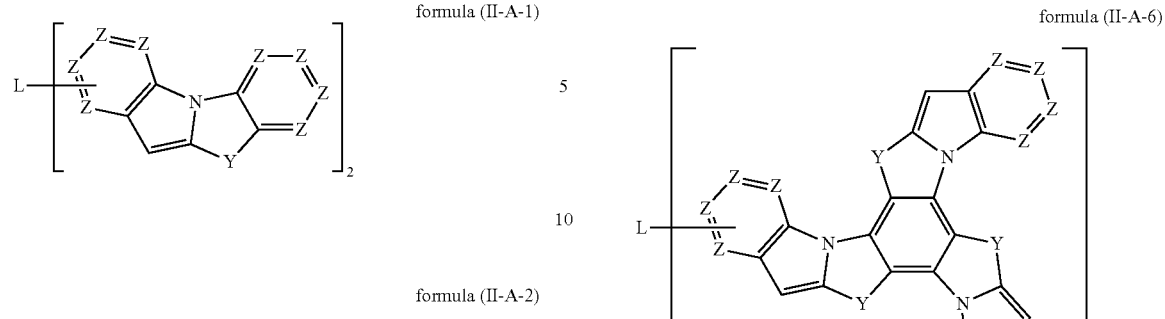
formula (II-A-7)
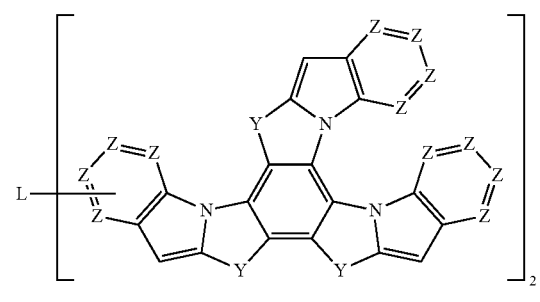
formula (II-B-1)
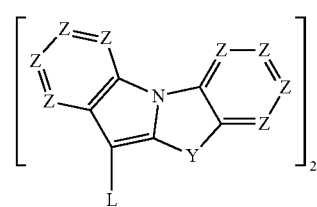
formula (II-B-2)
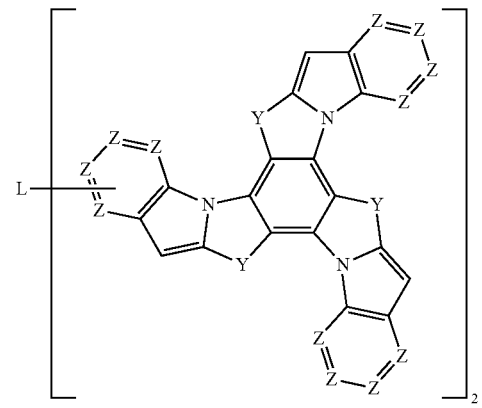
formula (II-B-3)
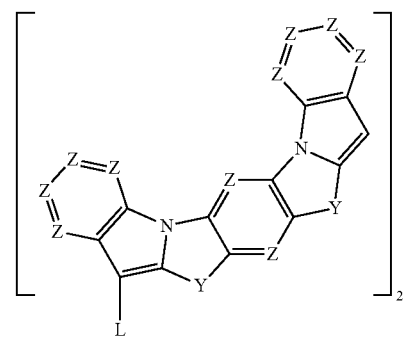

formula (II-B-4)

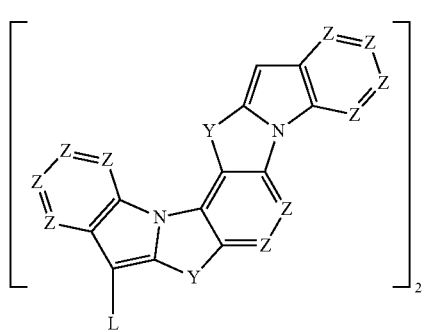

formula (II-B-5)

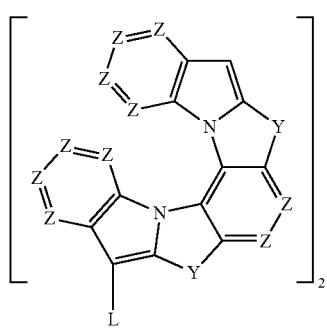

formula (II-B-6)

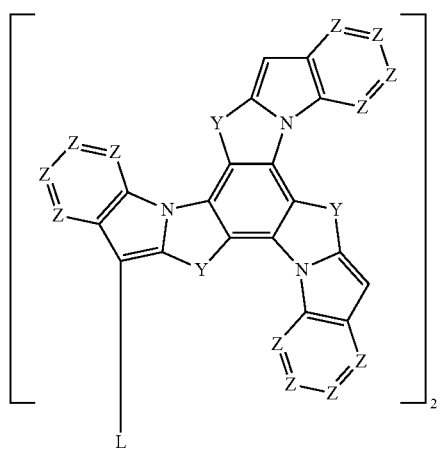

formula (II-B-7)

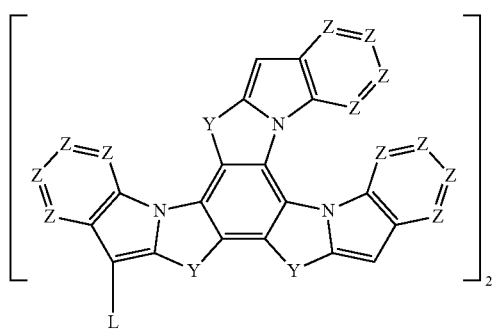

formula (II-C-1)

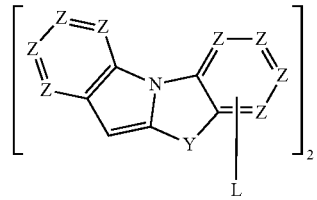

formula (II-C-2)

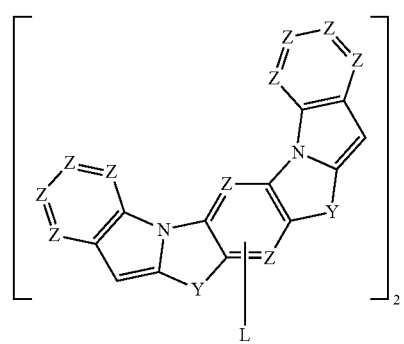

formula (II-C-3)

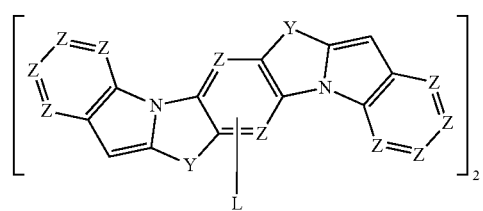

formula (II-C-4)

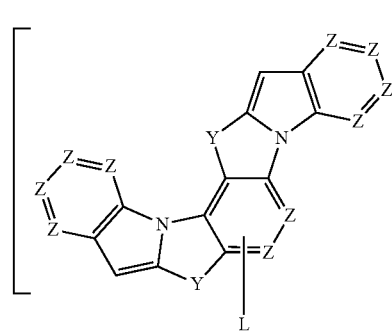

and formula (II-C-5)

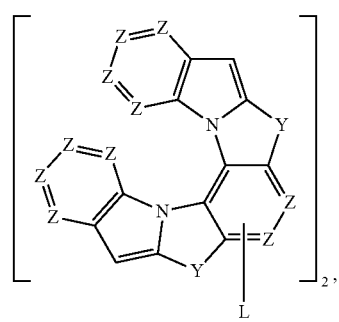

where the symbols occurring are as defined in claim 1 and the group Z to which the group L is bonded stands for a carbon atom, and where the compounds may be substituted by radicals $R^1$ at all unsubstituted positions.

8. The electronic device according to claim 1, wherein the device is selected from the group consisting of an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, an organic laser diode, and an organic electroluminescent device.

9. The electronic device according to claim 1, wherein the device is an organic electroluminescent device, wherein the compound of the formula (I) or (II) is present as hole-transport material in a hole-transport layer or hole-injection layer and/or is present as matrix material in an emitting layer and/or is present as electron-transport material in an electron-transport layer.

10. A compound of the formula (I) or (II),

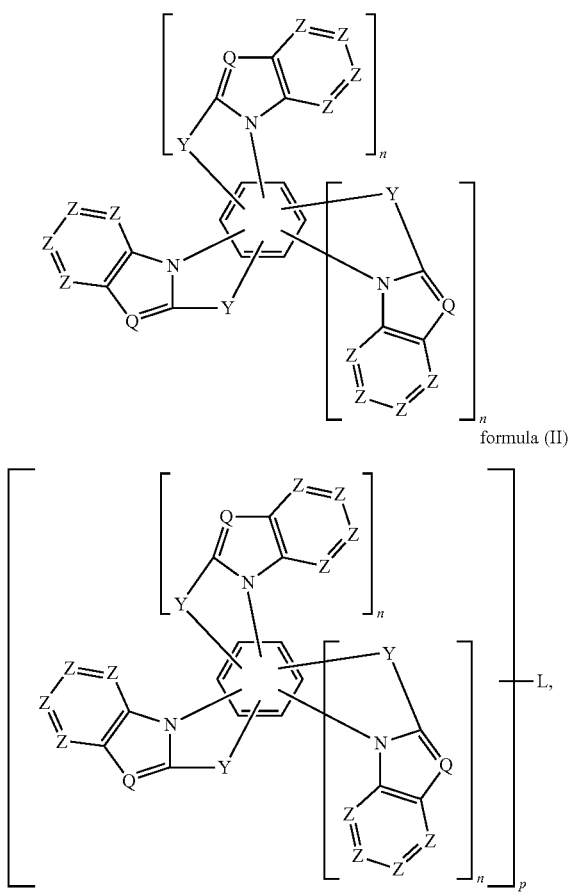

formula (I)

formula (II)

wherein:
Y is $C(R^1)_2$;
Z are on each occurrence, identically or differently, $CR^1$ or N;
Q is $CR^1$;
L is selected from C=O, C=$NR^1$, Si($R^1$)$_2$, $NR^1$, P(=O)($R^1$), O, S, SO, SO$_2$, alkylene groups having 1 to 20 C atoms or alkenylene or alkynylene groups having 2 to 20 C atoms, where one or more CH$_2$ groups in the said groups may be replaced by Si($R^1$)$_2$, O, S, C=O, C=$NR^1$, C(=O)O, (C=O)$NR^1$, $NR^1$, P(=O)($R^1$), SO or SO$_2$ and where one or more H atoms in the said groups may be replaced by D, F, Cl, Br, I, CN or NO$_2$, and aromatic or heteroaromatic ring systems having 5 to 60 aromatic ring atoms, which may in each case be substituted by one or more radicals $R^1$, and any desired combinations of 1, 2, 3, 4 or 5 identical or different groups selected from the above-mentioned groups; or L is a single bond, where p in this case is equal to 2;

$R^1$ is on each occurrence, identically or differently, H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy, heteroaryloxy, aralkyl or heteroaralkyl group having 5 to 60 aromatic ring atoms, which may be substituted by one or more radicals $R^2$;

$R^2$ is on each occurrence, identically or differently, H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —R$^3$C=CR$^3$—, —C≡C—, Si(R$^3$)$_2$, Ge(R$^3$)$_2$, Sn(R$^3$)$_2$, C=O, C=S, C=Se, C=NR$^3$, —C(=O)O—, —C(=O)NR$^3$—, NR$^3$, P(=O)(R$^3$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals $R^3$, or an aryloxy, heteroaryloxy, aralkyl or heteroaralkyl group having 5 to 60 aromatic ring atoms, which may be substituted by one or more radicals $R^3$, where two or more radicals $R^2$ may be linked to one another and may form a ring or a ring system;

$R^3$ is on each occurrence, identically or differently, H, D, F or an aliphatic, aromatic and/or heteroaromatic organic radical having 1 to 20 C atoms, in which, in addition, one or more H atoms may be replaced by D or F; two or more substituents $R^3$ here may also be linked to one another and form a ring or a ring system;

n is on each occurrence, identically or differently, 0 or 1, where, in the case n=0, the group in brackets is not present and optionally groups $R^1$ are instead bonded to the central benzene ring;

p is equal to 2, 3, 4, 5 or 6; and where the group Y and the nitrogen atom at any desired adjacent positions may be bonded to the aromatic six-membered ring;

where, in the formulae (I) and (II), in each case no or 1, 2 or 3 carbon atoms which are constituents of the central aromatic six-membered ring may be replaced by N if the sum of the indices n is equal to 0, and where, in the formulae (I) and (II), in each case no or 1 or 2 carbon atoms which are constituents of the central aromatic six-membered ring may be replaced by N if the sum of the indices n is equal to 1, and where, in formula (II), the moieties in square brackets with index p which are bonded to L may be identical or different; and where, in formula (II), the group L may be bonded at any desired position of the moiety in square brackets with index p;

and the following compounds are excluded:

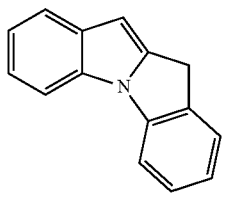

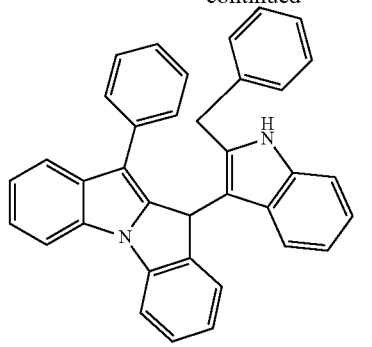

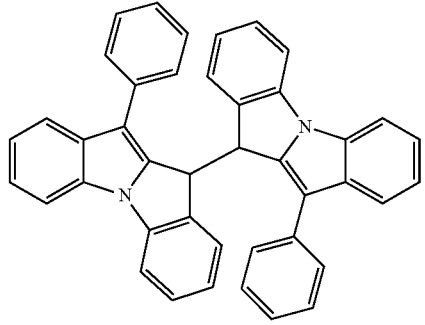

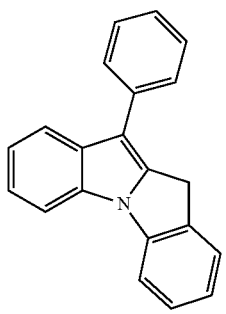

11. An oligomer, a polymer or a dendrimer comprising one or more compound according to claim 10, wherein one or more bond to the polymer, the oligomer or the dendrimer may be localised at any positions in formula (I) or (II) that are substituted by $R^0$ or $R^1$.

12. A formulation comprising at least one compound according to claim 10 and at least one solvent.

13. A formulation comprising at least one polymer, oligomer or dendrimer according to claim 11 and at least one solvent.

* * * * *